United States Patent
Emery et al.

(10) Patent No.: US 11,636,926 B1
(45) Date of Patent: Apr. 25, 2023

(54) JOINING PATIENT EHR DATA WITH COMMUNITY PATIENT DATA

(71) Applicant: ALLSCRIPTS SOFTWARE, LLC, Chicago, IL (US)

(72) Inventors: Brad Lucas Emery, Phoenixville, PA (US); Surj Kant Ramlogan, Canton, OH (US); Assaf Halevy, Pittsburgh, PA (US); Ellen Loch, Columbus, OH (US)

(73) Assignee: ALTERA DIGITAL HEALTH INC., Chicago, IL (US)

( * ) Notice: Subject to any disclaimer, the term of this patent is extended or adjusted under 35 U.S.C. 154(b) by 1156 days.

(21) Appl. No.: 14/588,408

(22) Filed: Dec. 31, 2014

Related U.S. Application Data

(60) Provisional application No. 61/943,489, filed on Feb. 23, 2014, provisional application No. 61/943,373, filed on Feb. 22, 2014.

(51) Int. Cl.
*G16H 10/60* (2018.01)
*G16H 50/70* (2018.01)

(52) U.S. Cl.
CPC ............ *G16H 10/60* (2018.01); *G16H 50/70* (2018.01)

(58) Field of Classification Search
CPC .............................. G06F 19/322; G16H 10/60
See application file for complete search history.

(56) References Cited

U.S. PATENT DOCUMENTS

| | | | |
|---|---|---|---|
| 6,684,188 B1 | 2/2004 | Mitchell et al. | |
| 6,904,161 B1 * | 6/2005 | Becker | G01S 7/52098 382/128 |
| 8,850,057 B2 * | 9/2014 | Natoli | H04L 45/00 709/232 |
| 9,202,084 B2 | 12/2015 | Moore | |
| 2003/0140044 A1 * | 7/2003 | Mok | G06Q 50/22 |
| 2005/0137929 A1 * | 6/2005 | Frazier | G06Q 10/0639 705/7.38 |
| 2005/0171762 A1 * | 8/2005 | Ryan | G06Q 50/22 704/200 |
| 2006/0095298 A1 * | 5/2006 | Bina | G06Q 10/06 705/2 |
| 2007/0194939 A1 * | 8/2007 | Alvarez | A61B 5/0002 340/573.1 |

(Continued)

*Primary Examiner* — John P Go
*Assistant Examiner* — Chad A Newton
(74) *Attorney, Agent, or Firm* — Calfee, Halter & Griswold LLP

(57) ABSTRACT

Providing healthcare services based on the combination of data from electronic healthcare records (EHRs) and community patient data includes: retrieving EHR data from an EHR database for a patient; retrieving community patient data for the patient; and providing clinical decision support for a healthcare provider at a computing device of the healthcare provider by interjecting, into a clinical workflow that utilizes the retrieved EHR data, the retrieved community patient data such that the clinical workflow utilizes the retrieved EHR data and the retrieved community patient data without importing the retrieved community patient data into the EHR database, and providing results of the workflow to the healthcare provider in a user interface at the computing device. The EHR data joined with the community patient data is actionable without importing the community patient data into the EHR database.

17 Claims, 43 Drawing Sheets

(56) References Cited

U.S. PATENT DOCUMENTS

| | | | |
|---|---|---|---|
| 2008/0120296 A1* | 5/2008 | Kariathungal | G06F 19/322 |
| 2008/0183536 A1* | 7/2008 | Hirabayashi | G06Q 10/06 |
| | | | 382/100 |
| 2009/0080408 A1* | 3/2009 | Natoli | H04L 45/00 |
| | | | 370/351 |
| 2009/0150812 A1* | 6/2009 | Baker | G16H 40/63 |
| | | | 715/764 |
| 2010/0088117 A1* | 4/2010 | Belden | G06F 19/321 |
| | | | 705/3 |
| 2012/0089419 A1* | 4/2012 | Uster | A61B 5/1115 |
| | | | 705/3 |
| 2014/0019617 A1* | 1/2014 | Hadar | G06F 9/45558 |
| | | | 709/225 |
| 2015/0127386 A1 | 5/2015 | Easterly | |

* cited by examiner

FIG. 3

*Illustration of User Interface of EHR Software in Which EHR Data and Community Healthcare Data of Patient are Combined and Presented for View and Interaction by User, i.e., Healthcare Provider*

| Alert Detail - HALL, ANGELA NICOLE | | | | | | Co |
|---|---|---|---|---|---|---|
| Alert Summary | | | | | | |
| Acknowle... | Viewed | Doc... | Alert | Priority | Type | |
| ✓ | ✓ | | Duplicate Order | HIGH | WARNING | |

Alert: Drug Interaction

Message: This following order is a duplicate of an existing order from the community record.

Expand     CT Head

*Example of Alert Regarding Duplicate Order to Order Existing in Community Records*

*Exemplary User Interface of EHR Software Showing LACE Scores for Patients, Population Health, and Events Due Alerts*

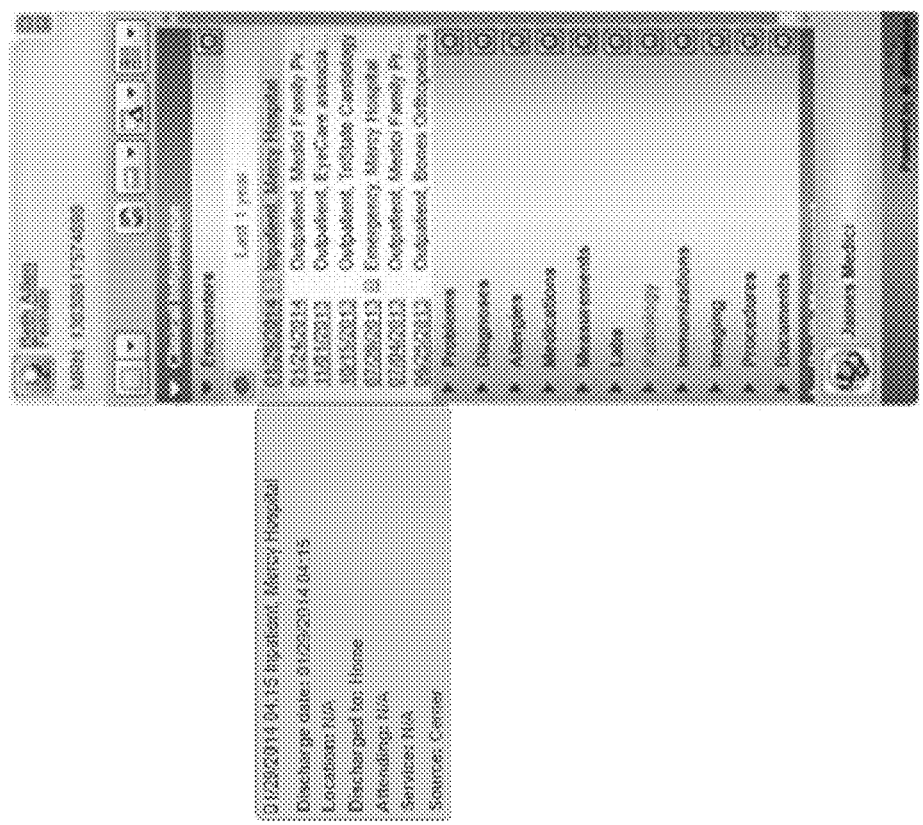
FIG. 22
FIG. 21
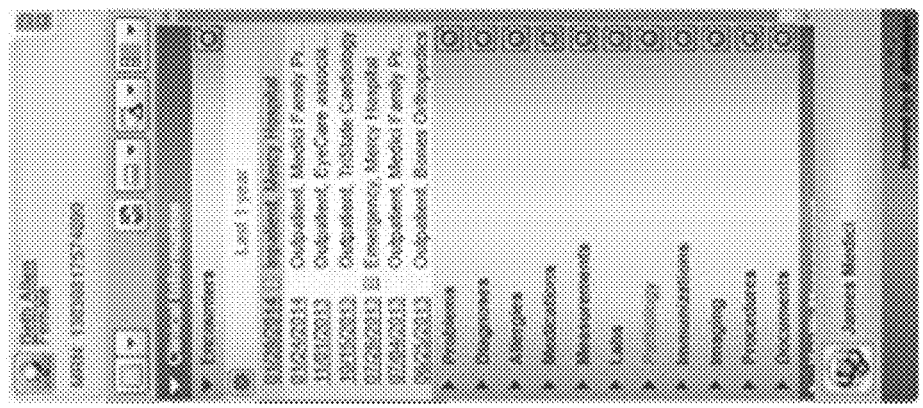
FIG. 20

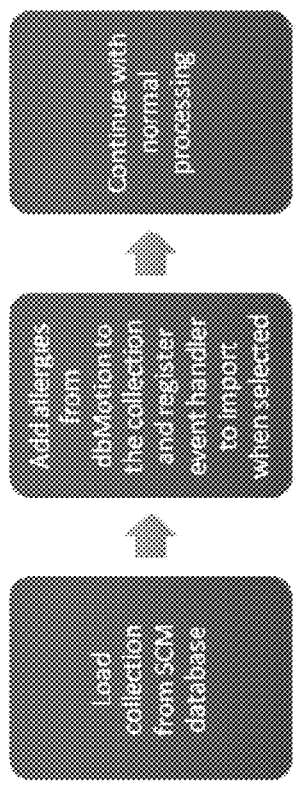
FIG. 43 Allergies Screen
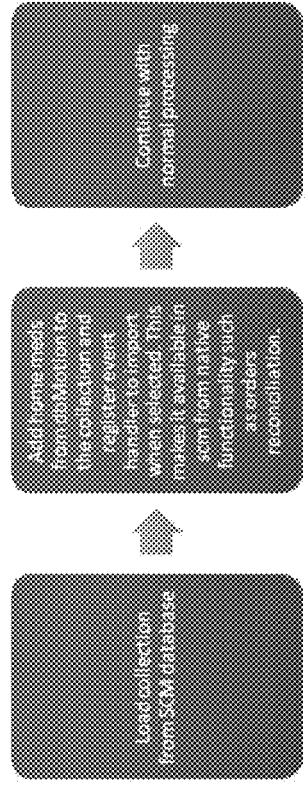
FIG. 44 Home Meds Screen
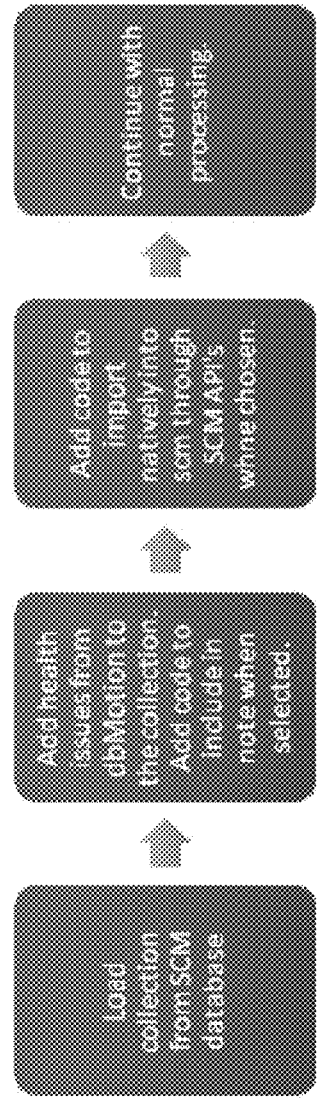
FIG. 45 Structured Notes Entry

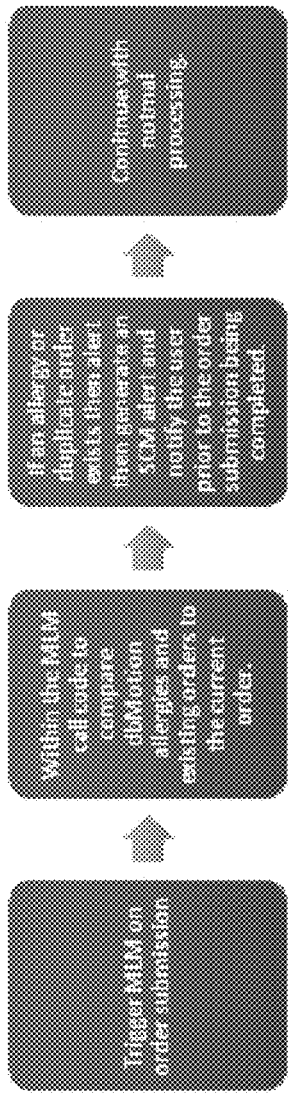
FIG. 46 — MLM's for Alerting
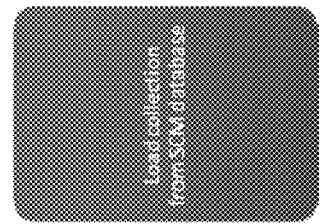
FIG. 47 — Document Tab Load
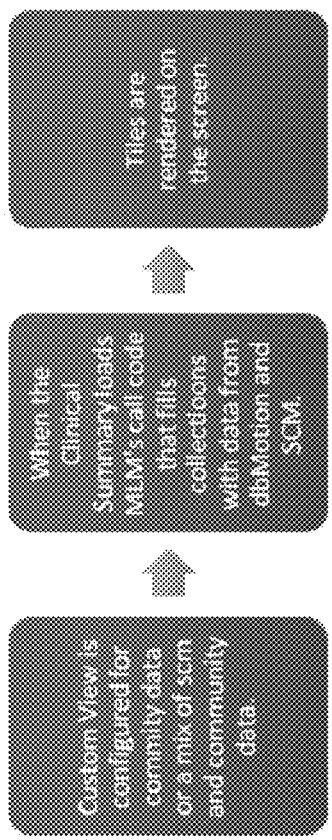
FIG. 48 — Clinical Summary Tiles

JOINING PATIENT EHR DATA WITH COMMUNITY PATIENT DATA

CROSS-REFERENCE TO RELATED APPLICATION

The present application is a U.S. nonprovisional patent application of, and claims priority under 35 U.S.C. § 119(e) to, each of U.S. provisional patent application 61/943,373, filed Feb. 22, 2014, which provisional patent application is incorporated by reference herein; and U.S. provisional patent application 61/943,489, filed Feb. 23, 2014, which provisional patent application is incorporated by reference herein. The present application hereby further incorporates herein by reference the entire disclosure of the Appendix attached hereto.

COPYRIGHT STATEMENT

All of the material in this patent document, including source code, is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

Having current and complete healthcare information about a patient when providing healthcare services to the patient is important. Often, healthcare information about a patient that is maintained in an EHR database used in an EHR system of a hospital or medical practitioner is incomplete, as other hospitals or medical practitioners may have provided healthcare services to the patient, the data regarding which would be in the particular EHR database used in the EHR system of such other hospitals or medical practitioners.

Efforts have been made to identify and obtain such "missing" information. For example, U.S. patent application publication 2012/0215560, which is hereby incorporated herein by reference, discloses, in at least some embodiments, apparatus, systems, and methods for identifying within the context of an EHR software user interface, to a healthcare provider using the EHR software, community patient information from other healthcare sources that may not be represented in the EHR system utilized by the healthcare provider. The healthcare provider is able to view the community patient information in a user interface provided by other than the EHR software and determine whether and which pieces of the community patient data, if any, to import into the EHR system being used by the healthcare provider and save such imported data in the patient's EHR in the EHR database of the EHR system being used by the healthcare provider. The user interface in which the community healthcare data is displayed basically 'sits' on top of the user interface provided by the EHR software.

A potential drawback to the apparatus, systems, and methods disclosed in this publication is that the patient community data may be overwhelming for the healthcare provider to review and identify what, if anything, to specifically import. Furthermore, such review requires time and additional effort, and many healthcare providers may not invest such time and effort as a practical matter; such healthcare providers may proceed on the premise that the EHR data is, in fact, complete.

Unfortunately, patient data in multiple places can negatively impact patient care if all pertinent information is unavailable to a healthcare provider at the point-of-care when decisions are being made. Having access to all available healthcare information for a patient can improve patient safety by eliminating, for example, duplicate prescriptions and reducing costs by eliminating duplicate tests. Indeed, it will be appreciated that alerting healthcare providers to things like allergies, drug interactions, duplicate medications, etc., from all sources improves patient safety.

In view of the foregoing, it is believed that a need exist for presenting patient data from all available sources (EHR database and community health sources alike) in a single user interface or otherwise in a single view and that doing so will significantly improve a healthcare provider's workflow by allowing the healthcare provider to remain in and interact with a single application, namely, the EHR software of the system being used by the healthcare provider. One or more aspects and features of the present invention are believed to address such perceived need. Moreover, it is believed that presenting data in this way, and making such data actionable, will reduce the need to import data into an EHR system, thereby saving time and effort of the healthcare provider, and facilitating decisions being made by the healthcare provider on more complete healthcare information about the patient.

SUMMARY OF THE INVENTION

The present invention generally relates to healthcare information technology, and in particular, to technology for and methods pertaining to joining or combining data from a patient's electronic healthcare record (EHR) maintained in a EHR database with community patient data for the patient without a need to import the community patient data into the EHR database. In this respect, one or more aspects and features of the present invention relate to joining data of an EHR computer system used by, for example, a healthcare provider, with data from multiple community healthcare information sources in such a way that the joined data appears native within—and is actionable within—the EHR computer system as if the joined data (and in particular, the data from the multiple community healthcare information sources) were native data in the EHR computer system.

Accordingly, in a first aspect of the present invention, a method of facilitating the provision of healthcare services based on the combination of data from electronic healthcare records (EHRs) that are maintained in an EHR database by a first party for a plurality of patients of the first party, and community patient data maintained in a second, different database and representing data that has been obtained from a plurality of different sources of electronic healthcare data, which sources are maintained by different third parties, includes the steps of: (a) retrieving EHR data from the EHR database for a subset of patients from the plurality of patients for whom EHR data is maintained in the EHR database, including receiving over a computer network the EHR data at a computing device of a healthcare provider; (b) retrieving community patient data, from the second database in which community patient data is maintained, for each of one or more patients of the subset of patients, including receiving over the computer network the community patient data at the computing device of the healthcare provider; and (c) providing, through a user interface on the computing device, access to healthcare information for the subset of patients for view by the healthcare provider on a display of the computing device, wherein the healthcare information comprises the retrieved EHR data joined with the retrieved community patient data, and wherein this is done without importing the retrieved community patient data into the EHR database. The joining is effected on the computing device in some embodiments, and is effected at the EHR database in other embodiments, such as at a server by which the EHR database is accessed.

In another aspect, a method of providing healthcare services based on the combination of data from electronic healthcare records (EHRs) that are maintained in an EHR database by a first party for a plurality of patients of the first party, and community patient data maintained in a second, different database and representing data that has been obtained from a plurality of different sources of electronic healthcare data, which sources are maintained by different third parties, includes the steps of: (a) retrieving EHR data from the EHR database for a subset of patients from the plurality of patients for whom EHR data is maintained in the EHR database, including receiving over a computer network the EHR data at a computing device of a healthcare provider; (b) retrieving community patient data for each of one or more patients of the subset of patients, including receiving over the computer network the community patient data at the computing device of the healthcare provider from the second database in which community patient data is maintained; and (c) providing, through a user interface on the computing device, access to healthcare information for the subset of patients for view by the healthcare provider on a display of the computing device, wherein the healthcare information comprises the retrieved EHR data joined with the retrieved community patient data, and wherein this is done without viewing and importing, by the healthcare provider, of community patient data into the EHR database. The joining is effected on the computing device in some embodiments, and is effected at the EHR database in other embodiments, such as at a server by which the EHR database is accessed.

In a feature of each of these two aspects, the method further comprises enabling the healthcare provider to exclude healthcare information for a particular patient from being viewed on the computing device which healthcare information originates from or comprises community patient data.

In a feature of each of these two aspects, said step (b) is performed for a particular patient when health information for the particular patient is to be displayed for view on the computing device by the healthcare provider.

In a feature of each of these two aspects, said step (b) is performed for a particular patient when health information for the particular patient first is to be displayed for view on the computing device; wherein the retrieved community patient information for the particular patient is stored in transient memory; and when needed thereafter and while still retained in the transient memory, the retrieved community patient data is read from the transient memory rather than being retrieved again from the second database. The transient memory preferably is transient memory of the computing device when the joining is effected on the computing device, and the transient memory preferably is transient memory of a server when the joining is effected at the EHR database or otherwise at a location remote to the computing device.

In a feature of each of these two aspects, steps (a) and (b) are performed concurrently for the subset of patients.

In a feature of each of these two aspects, steps (a) and (b) are performed before step (c) for the subset of patients.

In a feature of each of these two aspects, the user interface comprises a facility boards user interface for managing patients at a healthcare facility.

In a feature of each of these two aspects, the user interface comprises an orders user interface for reviewing and writing orders.

In a feature of each of these two aspects, the user interface comprises a results user interface for accessing results.

In a feature of each of these two aspects, the user interface comprises a documents user interface for accessing documents.

In a feature of each of these two aspects, the user interface comprises a visit record review interface for reviewing prior patient encounters.

In a feature of each of these two aspects, the user interface comprises a structured notes interface for documents a patient encounter.

In a feature of each of these two aspects, the user interface comprises a medication review user interface for reviewing medication of a patient.

In a feature of each of these two aspects, the user interface comprises an order reconciliation user interface for reviewing and writing orders for a patient.

In another aspect, a method of providing healthcare services based on the combination of data from electronic healthcare records (EHRs) that are maintained in an EHR database by a first party for a plurality of patients of the first party, and community patient data maintained in a second, different database and representing data that has been obtained from a plurality of different sources of electronic healthcare data, which sources are maintained by different third parties, includes the steps of: (a) retrieving EHR data from the EHR database for a subset of patients from the plurality of patients for whom EHR data is maintained in the EHR database, including receiving over a computer network the EHR data at a computing device of a healthcare provider; (b) retrieving community patient data for each of one or more patients of the subset of patients, including receiving over the computer network the community patient data at the computing device of the healthcare provider from the second database in which community patient data is maintained; (c) providing clinical decision support for the healthcare provider by intercepting a clinical workflow that utilizes the retrieved EHR data and interjecting into the clinical workflow the retrieved community patient data such that the clinical workflow utilizes the retrieved EHR data and the retrieved community patient data without importing the retrieved community patient data into the EHR database; and (d) providing, through a user interface on the computing device, results of the clinical workflow for view by the healthcare provider.

In a feature of this aspect, the method further comprises enabling the healthcare provider to exclude the community patient data from being interjected into the clinical workflow.

In a feature of this aspect, the clinical workflow comprises prescribing an order and wherein the method further comprises generating an alert if the order is a duplicate of an order found in the retrieved community patient data.

In a feature of this aspect, the clinical workflow comprises prescribing medication and wherein the method further comprises generating an alert if the medication prescribed conflicts with medication of the patient found in the retrieved community patient data, or if the patient is found to have an allergy to the medication.

In a feature of this aspect, said step (b) is performed when a clinical workflow is initiated.

In a feature of this aspect, steps (a) and (b) are performed concurrently for the subset of patients.

In a feature of this aspect, steps (a) and (b) are performed before step (c) for the subset of patients.

In a feature of the foregoing aspects, the user interface on the computing device through which access is provided to the joined data is generated by an EHR software program running on the computing device.

In a feature of the foregoing aspects, the user interface on the computing device through which access is provided to the joined data is generated by a first software program running on the computing device, and wherein the method further comprises providing, for review by the healthcare provider, through a user interface comprising an EHR agent that is generated by a second, different software program running on the computing device, the retrieved community patient data without any EHR data retrieved from the EHR database.

In a feature of the foregoing aspects, said step (a) comprises communicating one or more database queries to the EHR database.

In a feature of the foregoing aspects, said step (b) comprises communicating one or more database queries to the second database.

In a feature of the foregoing aspects, the second database represents a consolidation of the plurality of different sources of electronic healthcare data maintained by the different third parties.

In a feature of the foregoing aspects, the second database further represents data that has been obtained from an additional source in which patient data is maintained by patients themselves. In some embodiments, the patient data for each patient that is maintained in the additional source is retrieved on a patient basis from each of a plurality of different data sources maintained by different third parties. Moreover, at least one such third party is a healthcare organization.

In a feature of the foregoing aspects, the subset of patients consists of a single patient.

In a feature of the foregoing aspects, the subset of patients comprises a plurality of patients.

In a feature of the foregoing aspects, the method further comprises filtering out retrieved community patient data based on the retrieved EHR data for avoiding duplicate information. Furthermore, the method may further comprise identifying duplicate information by reference to a semantic dictionary.

In a feature of the foregoing aspects, the method further comprises filtering out retrieved community patient data based on the retrieved EHR data for avoiding duplicate information.

In a feature of the foregoing aspects, the retrieved community patient data for each patient of the subset is not imported into the EHR record of the patient that is maintained in the EHR database.

In a feature of the foregoing aspects, the retrieved community patient data is stored in transient memory of the computing device upon being received over the computer network from the second database, and is lost when the computing device is powered off.

In a feature of the foregoing aspects, the method further comprises again retrieving community patient data for a patient of the subset of patients after a predetermined period of time for refreshing of the community patient data stored in transient memory of the computing device. Furthermore, the community patient data may be is refreshed after a period of time comprising a day.

In a feature of the foregoing aspects, the method further comprises again retrieving community patient data for a patient of the subset of patients upon receiving user input instructing that the community patient data stored in transient memory of the computing device be refreshed.

In a feature of the foregoing aspects, the second database comprises a health information exchange (HIE) and is provided by a second party different from the first party and third parties.

In a feature of the foregoing aspects, community patient data in the second database is stored in universal health records for patients, and wherein the EHR records have a data structure for storing data for patients that is different from the data structure of the universal healthcare records.

In a feature of the foregoing aspects, the method is performed when providing healthcare services by the healthcare provider at a point-of-care.

In a feature of the foregoing aspects, the method further comprises visually indicating that healthcare information for a particular patient originates from or comprises community patient data. The method also may further comprise indicating the source of the community patient data.

In a feature of the foregoing aspects, one or more third parties each comprises a hospital.

In a feature of the foregoing aspects, one or more third parties each comprises a private medical practice.

In a feature of the foregoing aspects, one or more third parties each comprises a healthcare organization.

In a feature of the foregoing aspects, one or more third parties each comprises an accountable care organization (ACO).

In a feature of the foregoing aspects, the healthcare provider is a physician; a nurse practitioner; a surgeon; or a paramedic.

In another feature, the first party and at least one of the third parties are part of the same healthcare system, but use different or separate EHR computer systems.

In additional aspects, a non-transitory computer-readable medium contains computer-executable instructions that, when executed by a processor of a computing device, perform a method in accordance with one or more of the foregoing aspects.

In yet additional aspects, a computing device used by a healthcare provider when providing healthcare services to a patient, comprises a processor, display, and a non-transitory computer-readable medium having computer-executable instructions that, when executed by a processor of a computing device, perform a method in accordance with one or more of the foregoing aspects.

In another aspect, a method of facilitating the provision of healthcare services based on the combination of data from electronic healthcare records (EHRs) that are maintained in an EHR database by a first party for a plurality of patients of the first party, and community patient data maintained in a second, different database and representing data that has been obtained from a plurality of different sources of electronic healthcare data, which sources are maintained by different third parties, includes the steps of: (a) retrieving community patient data for a patient for whom EHR data is maintained in the EHR database, including receiving over a computer network the community patient data at a computing device of a healthcare provider from the second database in which community patient data is maintained; and (b) providing, through a user interface on the computing device, access to healthcare information for the patient for view by the healthcare provider on a display of the computing device, wherein the healthcare information comprises EHR data that is maintained in the EHR database joined with the retrieved community patient data, the joining being effected on the computing device without importing the retrieved community patient data into the EHR database.

In another aspect, a method of facilitating the provision of healthcare services based on the combination of data from electronic healthcare records (EHRs) that are maintained in an EHR database by a first party for a plurality of patients of the first party, and community patient data maintained in a second, different database and representing data that has been obtained from a plurality of different sources of electronic healthcare data, which sources are maintained by different third parties, includes the steps of: (a) retrieving community patient data for a patient for whom EHR data is maintained in the EHR database, including receiving over a computer network the community patient data at a computing device of a healthcare provider from the second database in which community patient data is maintained; and (b) providing, through a user interface on the computing device, access to healthcare information for the patient for view by the healthcare provider on a display of the computing device, wherein the healthcare information comprises EHR data that is maintained in the EHR database joined with the retrieved community patient data, the joining being effected on the computing device without viewing and importing, by the healthcare provider, of community patient data into the EHR database.

In yet another aspect, a method of facilitating the provision of healthcare services based on the combination of data from electronic healthcare records (EHRs) that are maintained in an EHR database by a first party for a plurality of patients of the first party, and community patient data maintained in a second, different database and representing data that has been obtained from a plurality of different sources of electronic healthcare data, which sources are maintained by different third parties, the method comprising the steps of: (a) retrieving community patient data for a patient for whom EHR data is maintained in the EHR database, including receiving over a computer network the community patient data at a computing device of a healthcare provider from the second database in which community patient data is maintained; (b) providing clinical decision support for the healthcare provider by intercepting a clinical workflow that utilizes EHR data maintained in the EHR database and interjecting into the clinical workflow the retrieved community patient data such that the clinical workflow utilizes EHR data maintained in the EHR database and the retrieved community patient data without importing the retrieved community patient data into the EHR database; and (c) providing, through a user interface on the computing device, results of the clinical workflow for view by the healthcare provider.

Another aspect includes a non-transitory computer-readable medium having computer-executable instructions that, when executed by a processor of a computing device, perform a method in accordance with at least one of the foregoing three aspects.

In another aspect, a method for determining risk of readmission of a patient if discharged from a healthcare facility includes the steps of: (a) retrieving community patient data for a patient from a database in which community patient data is maintained, and for whom EHR data is maintained by the healthcare facility in an EHR database, including receiving over a computer network the community patient data at a computing device of the healthcare facility; (b) calculating value representing a risk of readmission of the patient based on a combination of EHR data maintained in the EHR database and the retrieved community patient data without importing the retrieved community patient data into the EHR database; and (c) displaying, through a user interface on a display operably connected to the computing device, the calculated value score for the patient for view by healthcare providers on the display. The value calculated is preferably is a LACE score.

Another aspect includes a non-transitory computer-readable medium having computer-executable instructions that, when executed by a processor of a computing device, perform a method in accordance with at least one of the foregoing aspect.

In another aspect, a method of providing healthcare services based on the combination of data from electronic healthcare records (EHRs) that are maintained in an EHR database by a first party for a plurality of patients of the first party, and community patient data maintained in a second, different database and representing data that has been obtained from a plurality of different sources of electronic healthcare data, which sources are maintained by different third parties, includes the steps of: (a) retrieving EHR data from the EHR database for a subset of patients from the plurality of patients for whom EHR data is maintained in the EHR database, including receiving over a computer network the EHR data of a healthcare provider; (b) retrieving community patient data for each of one or more patients of the subset of patients, including receiving over the computer network the community patient data from the second database in which community patient data is maintained; (c) providing clinical decision support for the healthcare provider by intercepting a clinical workflow and interjecting into the clinical workflow the retrieved community patient data such that the clinical workflow utilizes the retrieved EHR data and the retrieved community patient data without importing the retrieved community patient data into the EHR database; and (d) providing, through a user interface on the computing device, results of the clinical workflow for view by the healthcare provider.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

With reference now to the drawings, the following is a brief description thereof.

FIG. 3 illustrates a user interface of exemplary EHR software, wherein medication summary information is displayed.

FIG. 4 illustrates an exemplary alert regarding a duplicate order that has been identified by the EHR software based on joined EHR data and community patient data.

FIG. 5 illustrates a user interface for a "Facility Board" tab in the exemplary EHR software, wherein as shown, healthcare information for a number of patients is presented.

Figure 7:
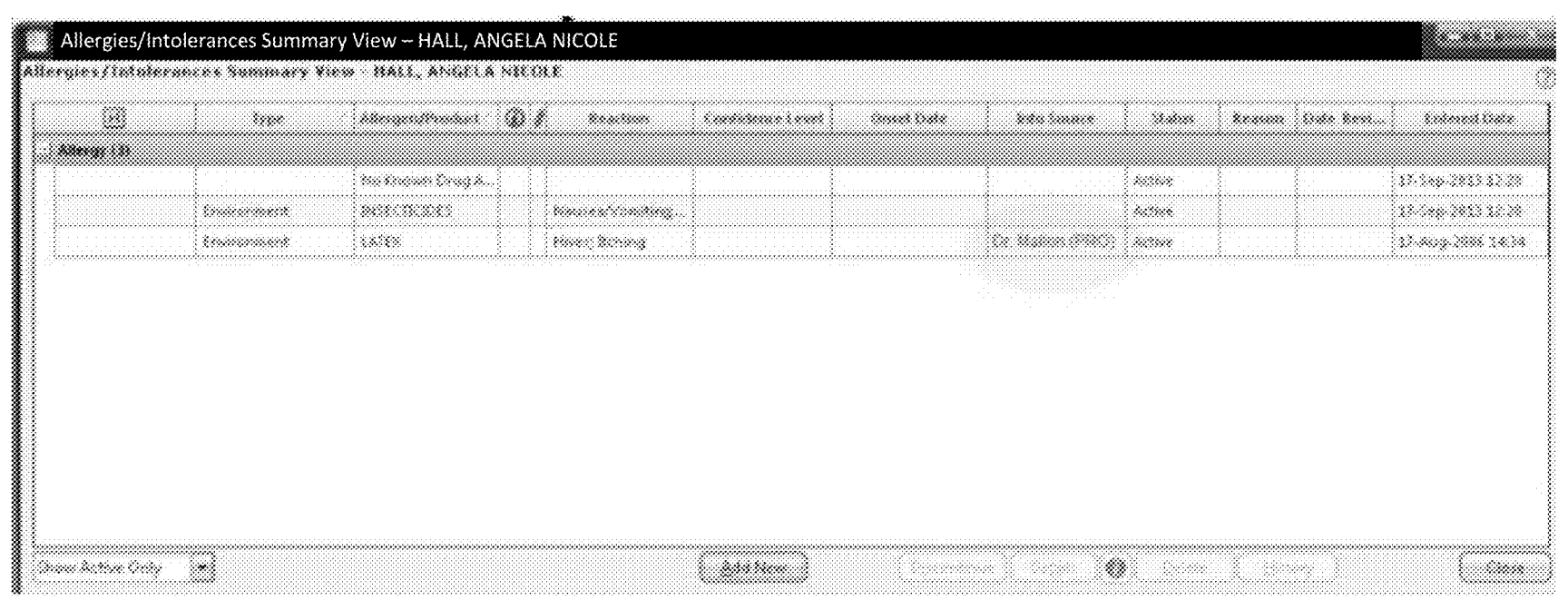

FIG. 7 illustrates a view for a particular patient of an "Allergies/Intolerances Summary View" user interface window of the exemplary EHR software.

Figure 14:
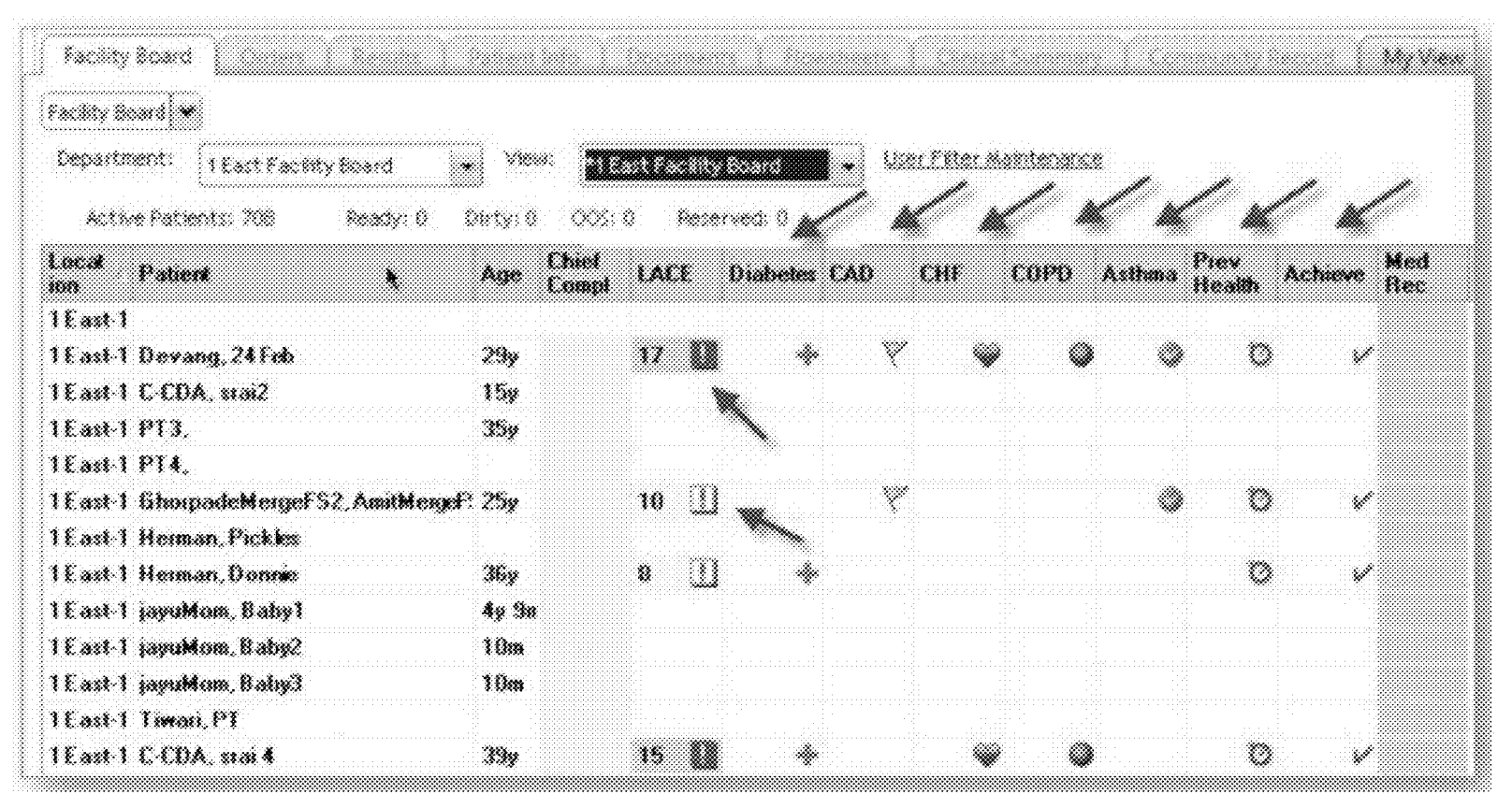

FIG. 14 illustrates a "Facility Board" Tab view of portion of a user interface window of the exemplary EHR software.

FIG. 15 illustrates the "Facility Board" Tab view within the overall context user interface window of the exemplary EHR software.

FIG. 17 illustrates another screenshot in which the smart agent user interface is utilized with the user interface window of FIG. 15.

FIG. 18 illustrates another screenshot in which the smart agent user interface is utilized with the user interface window of FIG. 15.

FIG. 19 illustrates another screenshot in which the smart agent user interface is utilized with the user interface window of FIG. 15; the smart agent user interface can be minimized and moved around within the display, and information can be expanded or collapsed for selected patients, as collectively shown in FIGS. 16-19. It will be noted that the smart agent has been minimized or closed in the view of FIG. 15.

FIGS. 20-22 illustrate the expandability of the smart agent as represented in FIGS. 16-19, with the user interface window of FIG. 15 being omitted for clarity of illustration.

Figure 23:
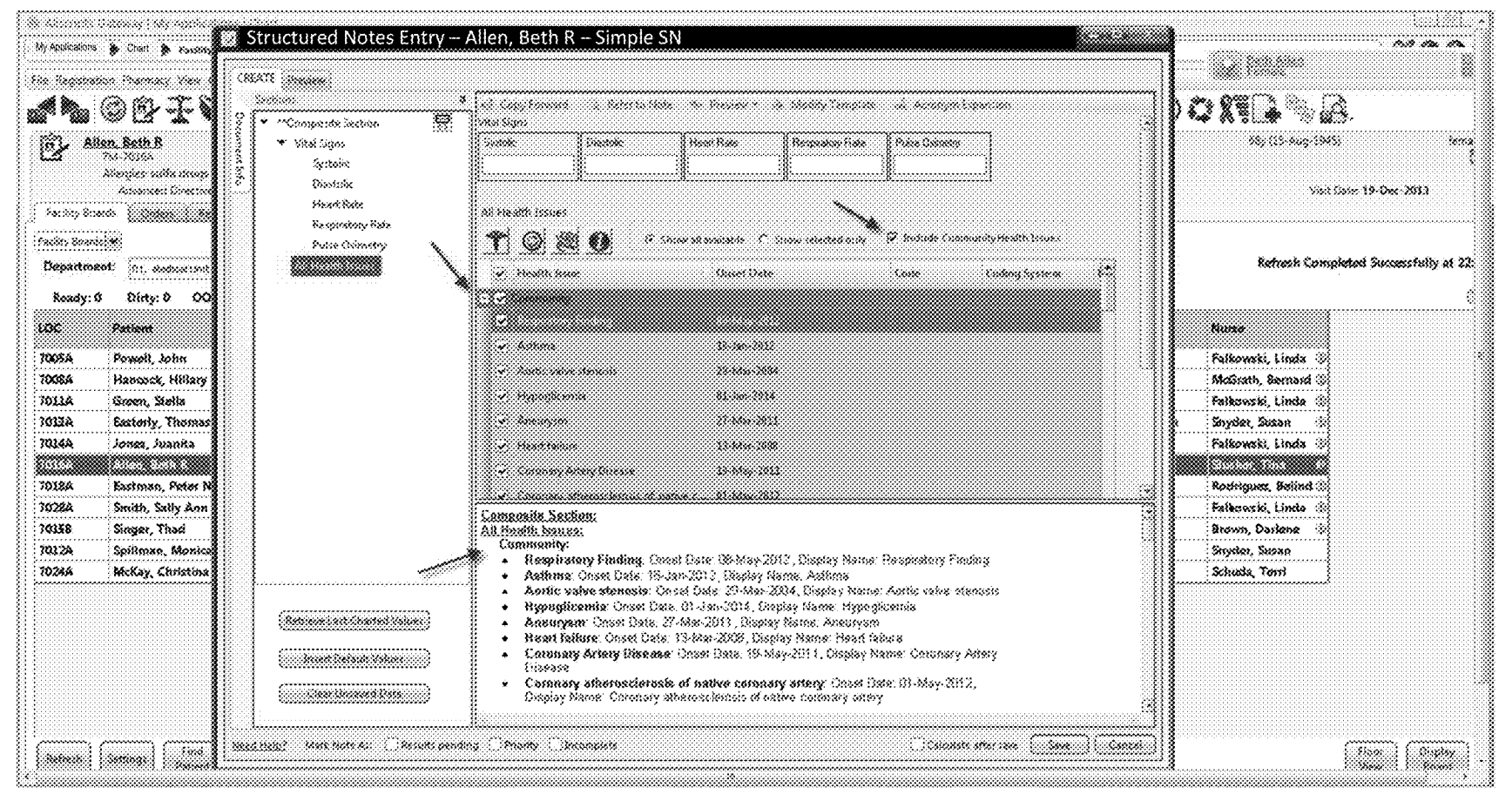
Figure 24:
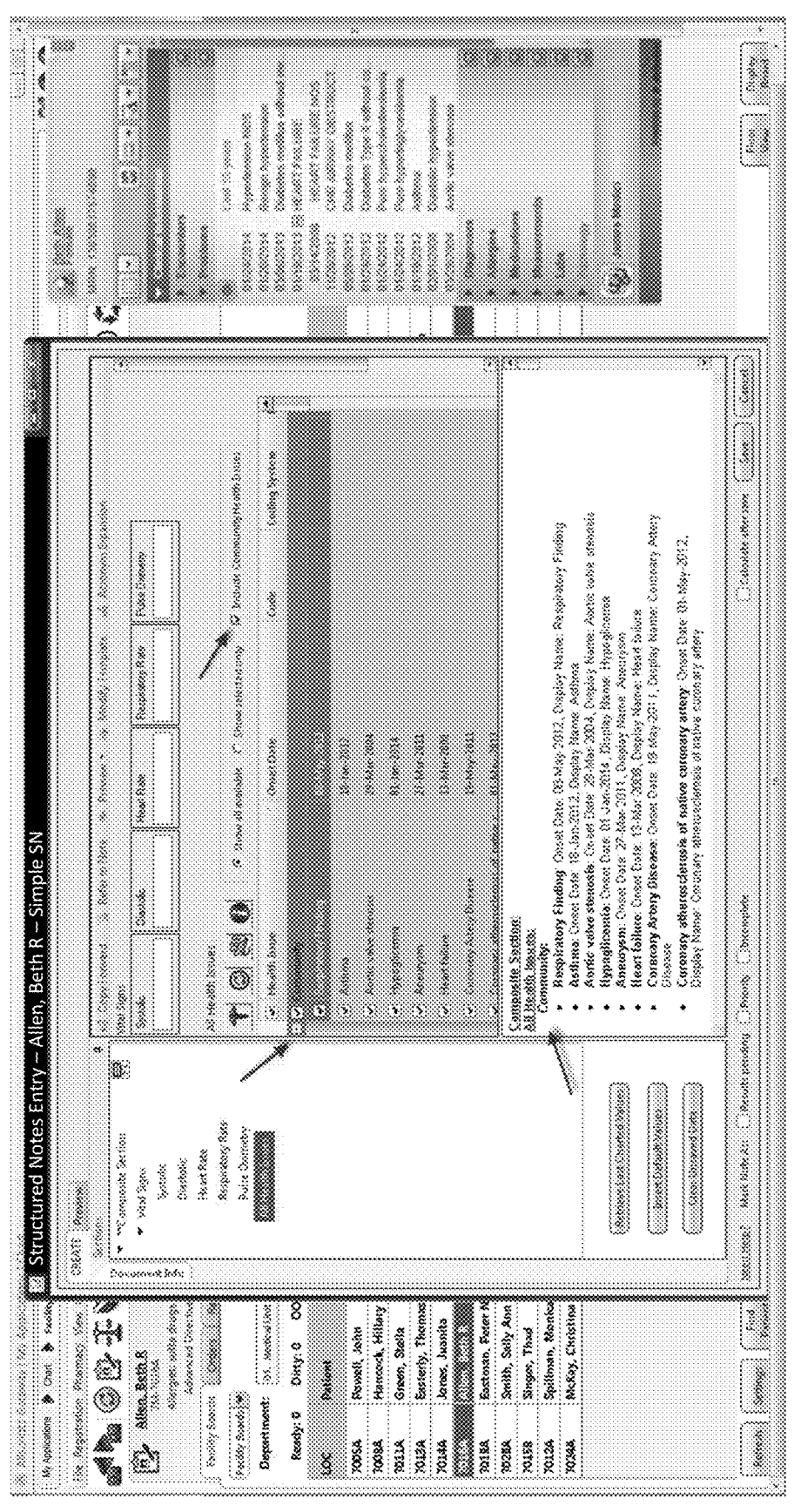
Figure 25:
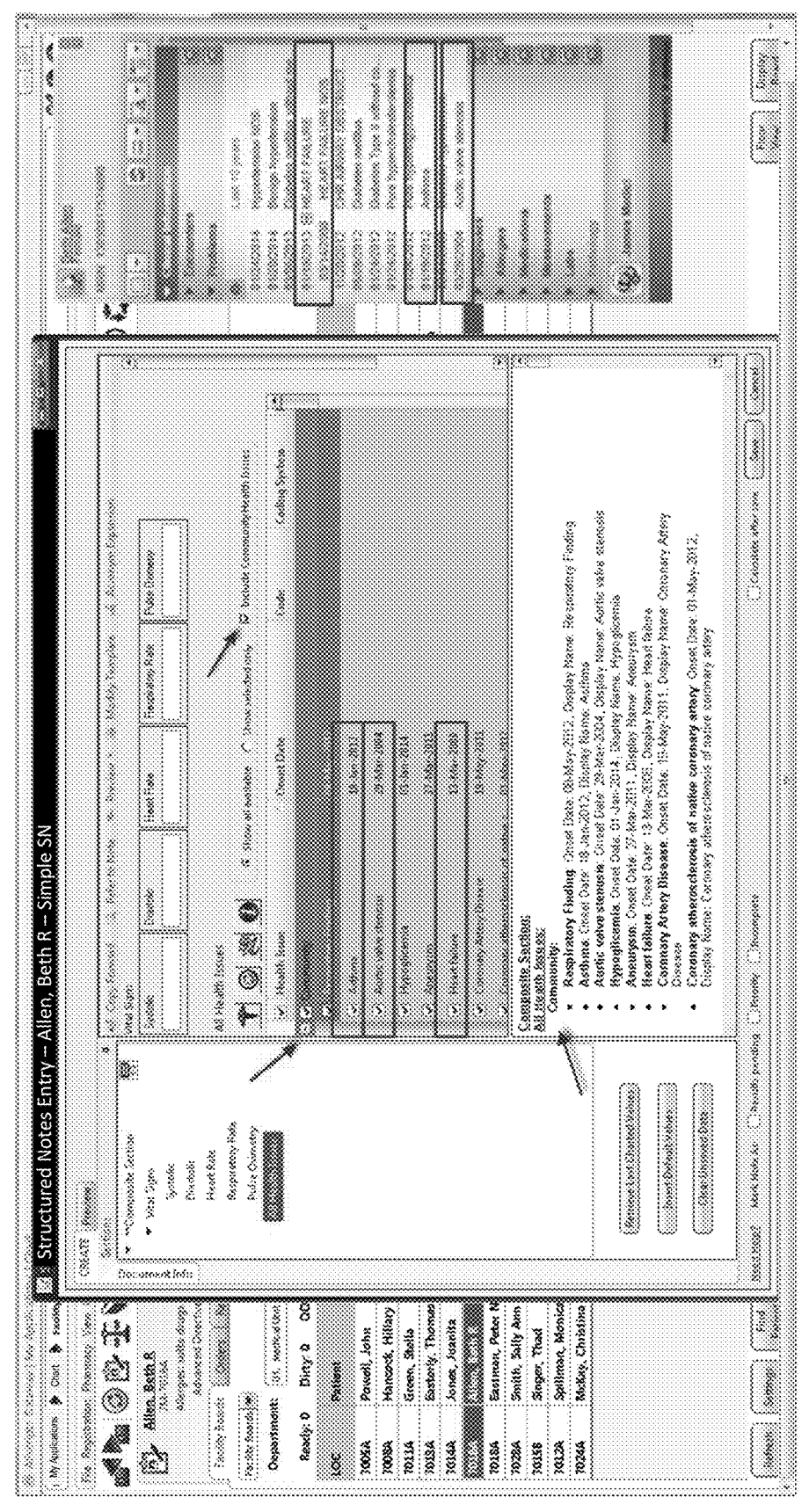
Figure 26:
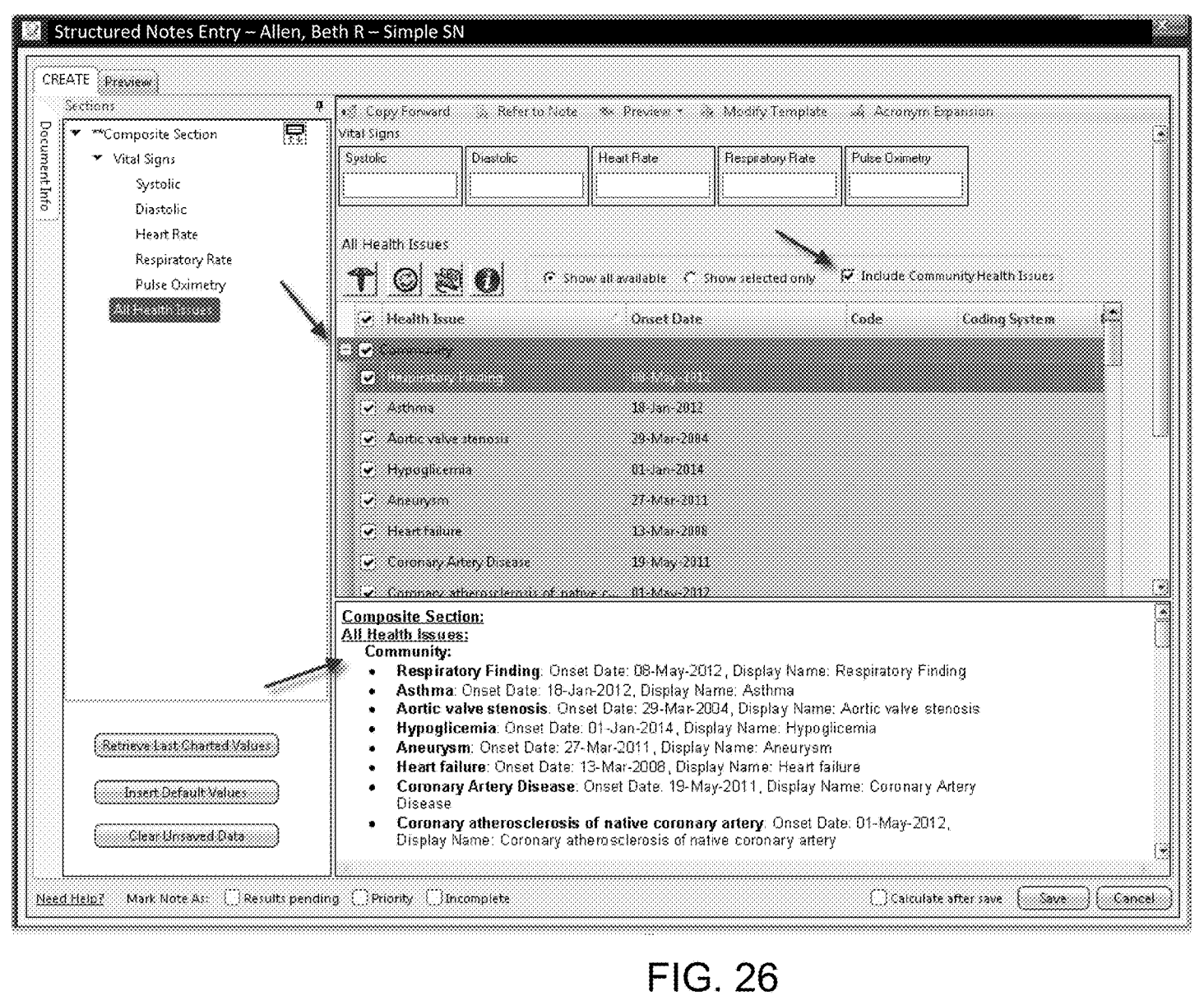
Figure 27:
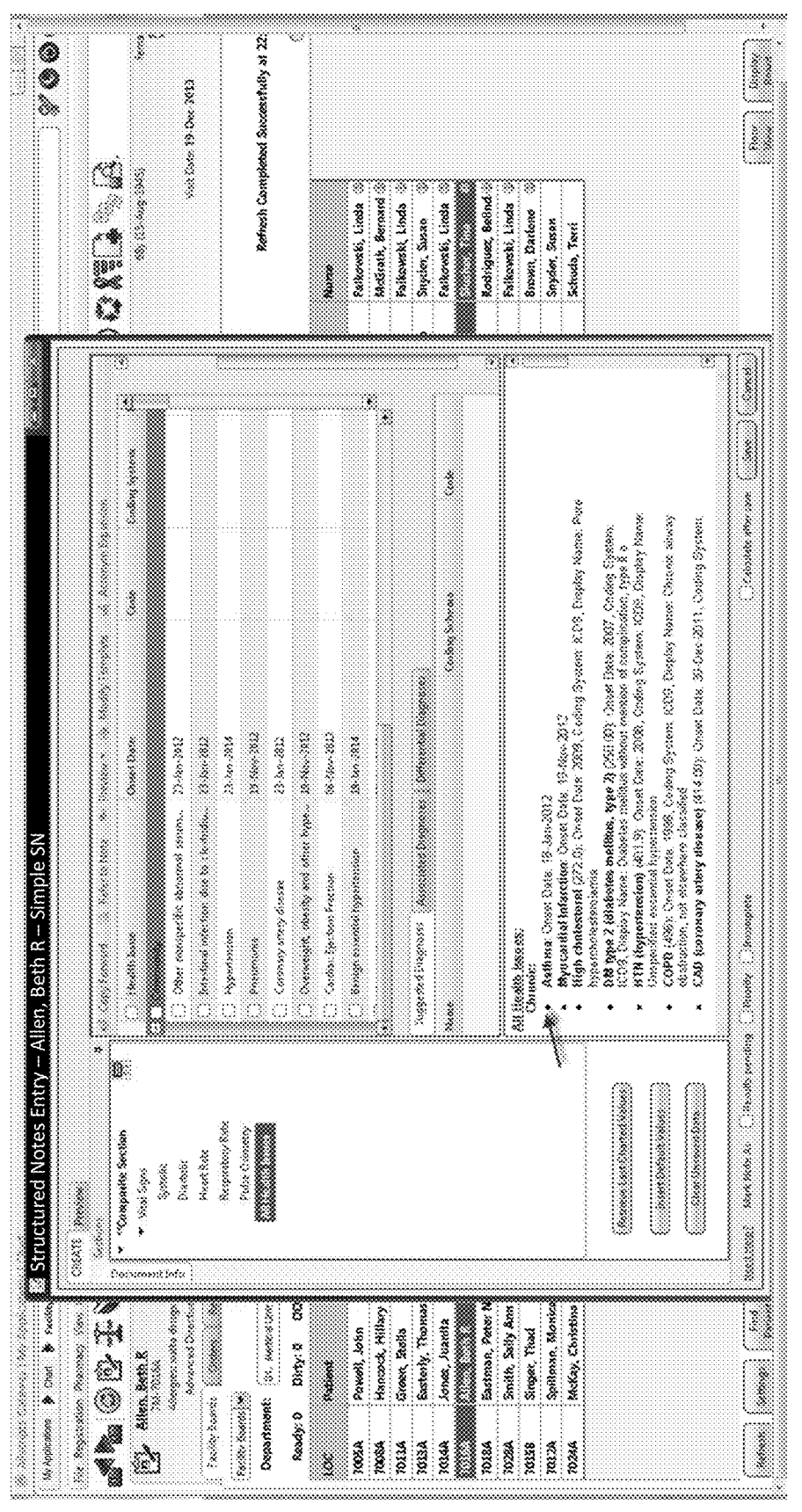
Figure 28:
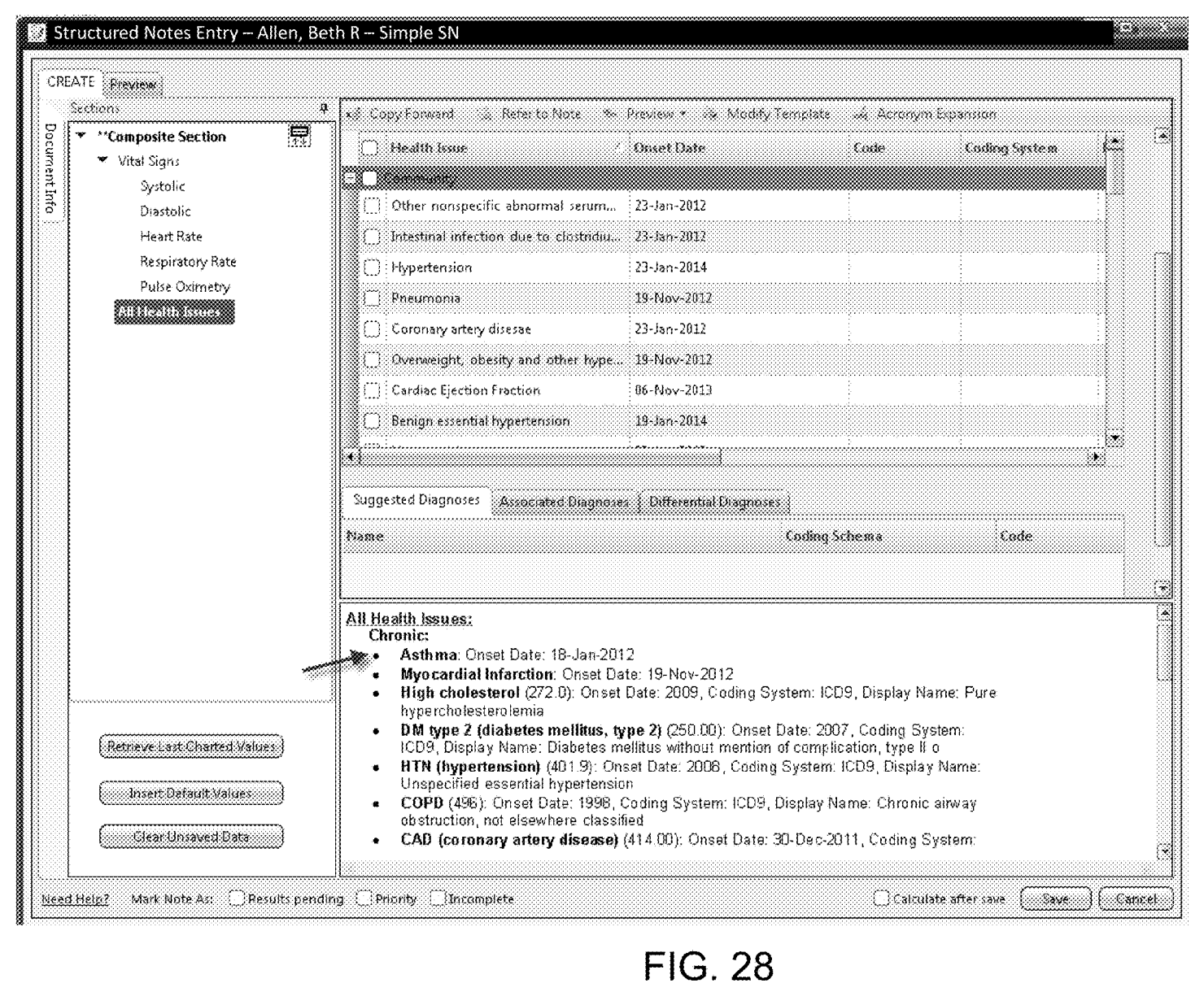

FIGS. 23-28 illustrate a structured notes user interface of the exemplary EHR software.

Figure 31:
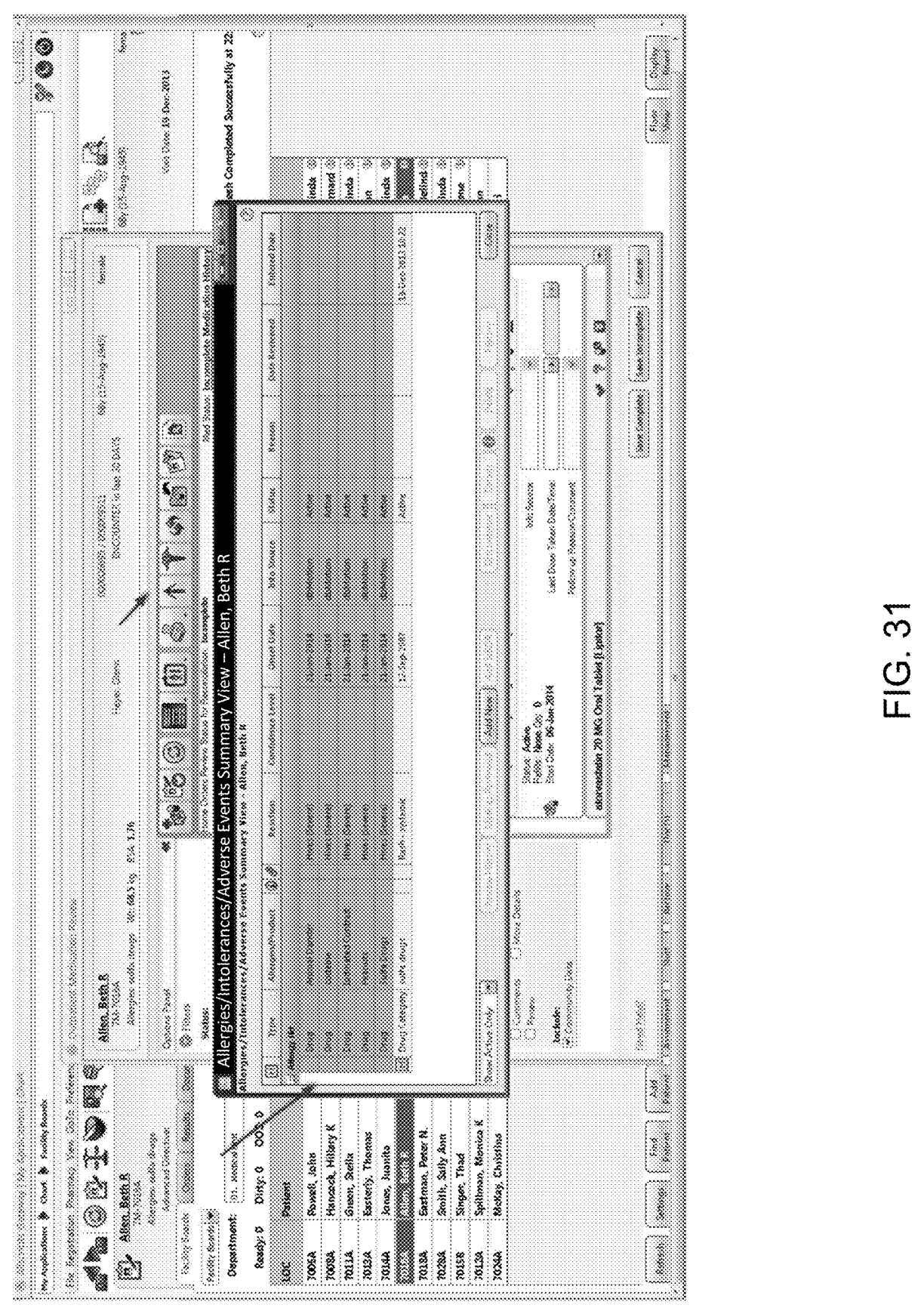

FIG. 31 illustrates an "Allergies/Intolerances/Adverse Events Summary View" user interface window for the selected patient in the user interface of FIG. 29.

Figure 32:
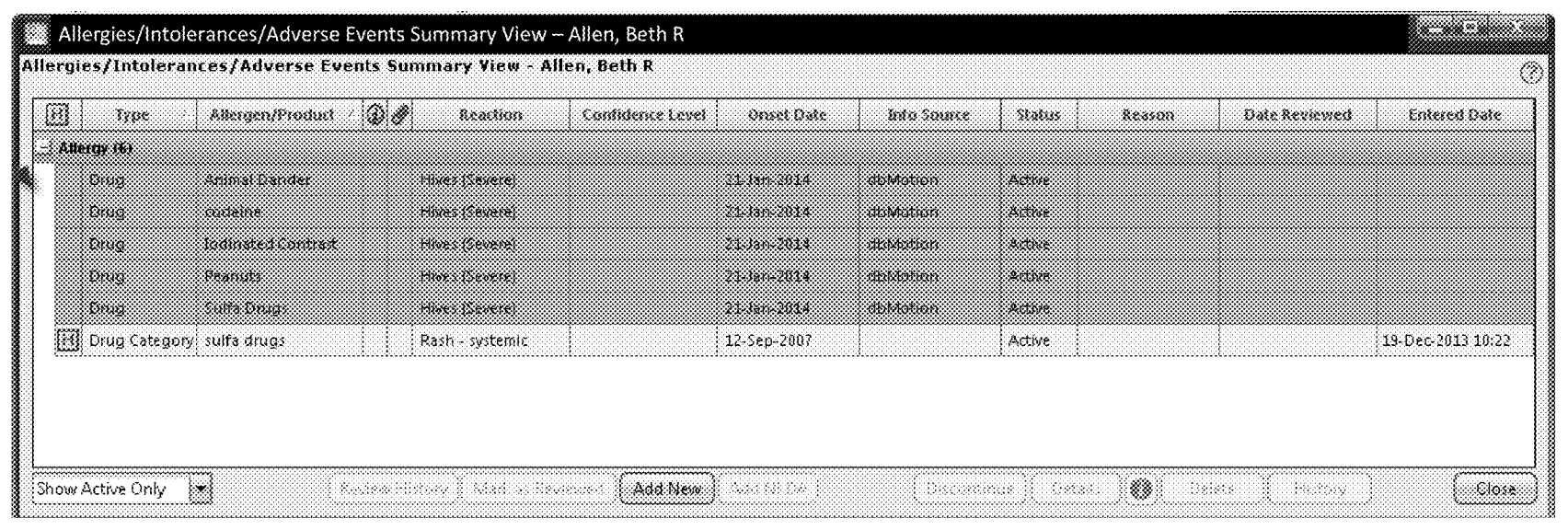

FIG. 32 illustrates just the "Allergies/Intolerances/Adverse Events Summary View" user interface window of FIG. 31 for clarity.

Figure 34:
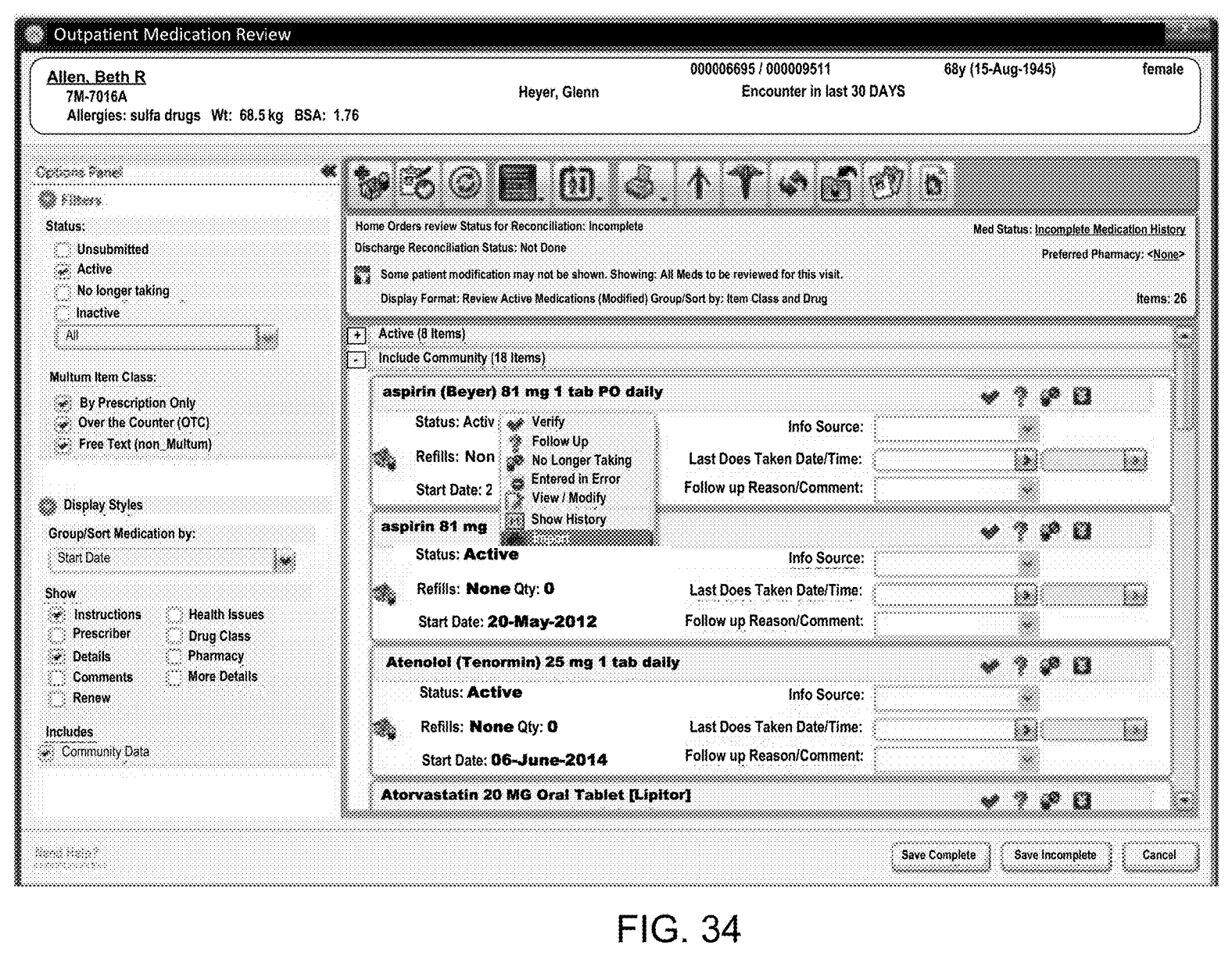

FIG. 34 illustrates just the "Outpatient Medication Review" user interface window of FIG. 33 for clarity.

FIG. 40 illustrates another view of the "Facility Board" tab view within the overall context user interface window of the exemplary EHR software, similar to the view of FIG. 39.

Figure 41:
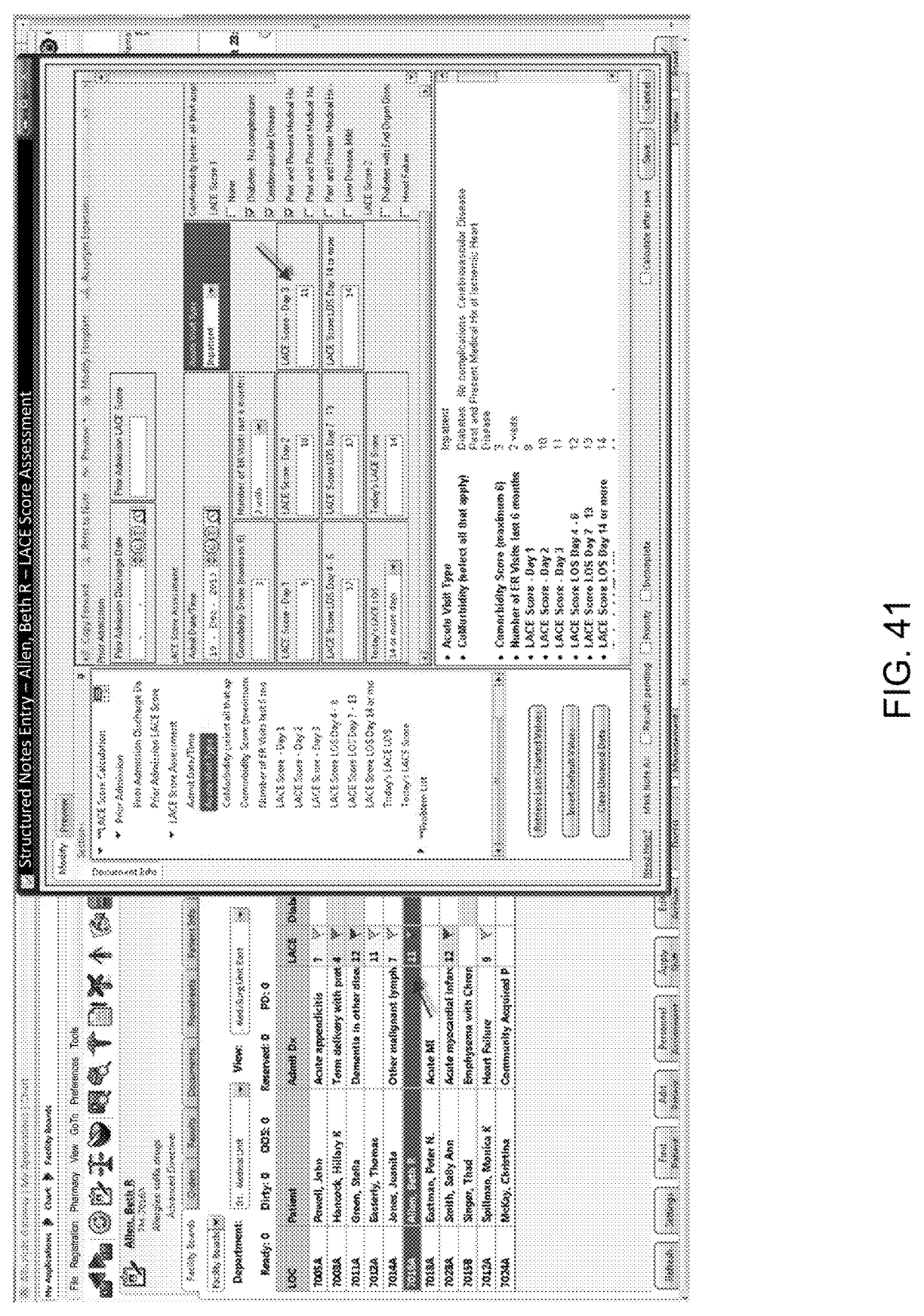

FIG. 41 illustrates a view of a "Structured Notes Entry" user interface window associated with the selected patient in the "Facility Board" Tab view of FIG. 40.

Figure 42:
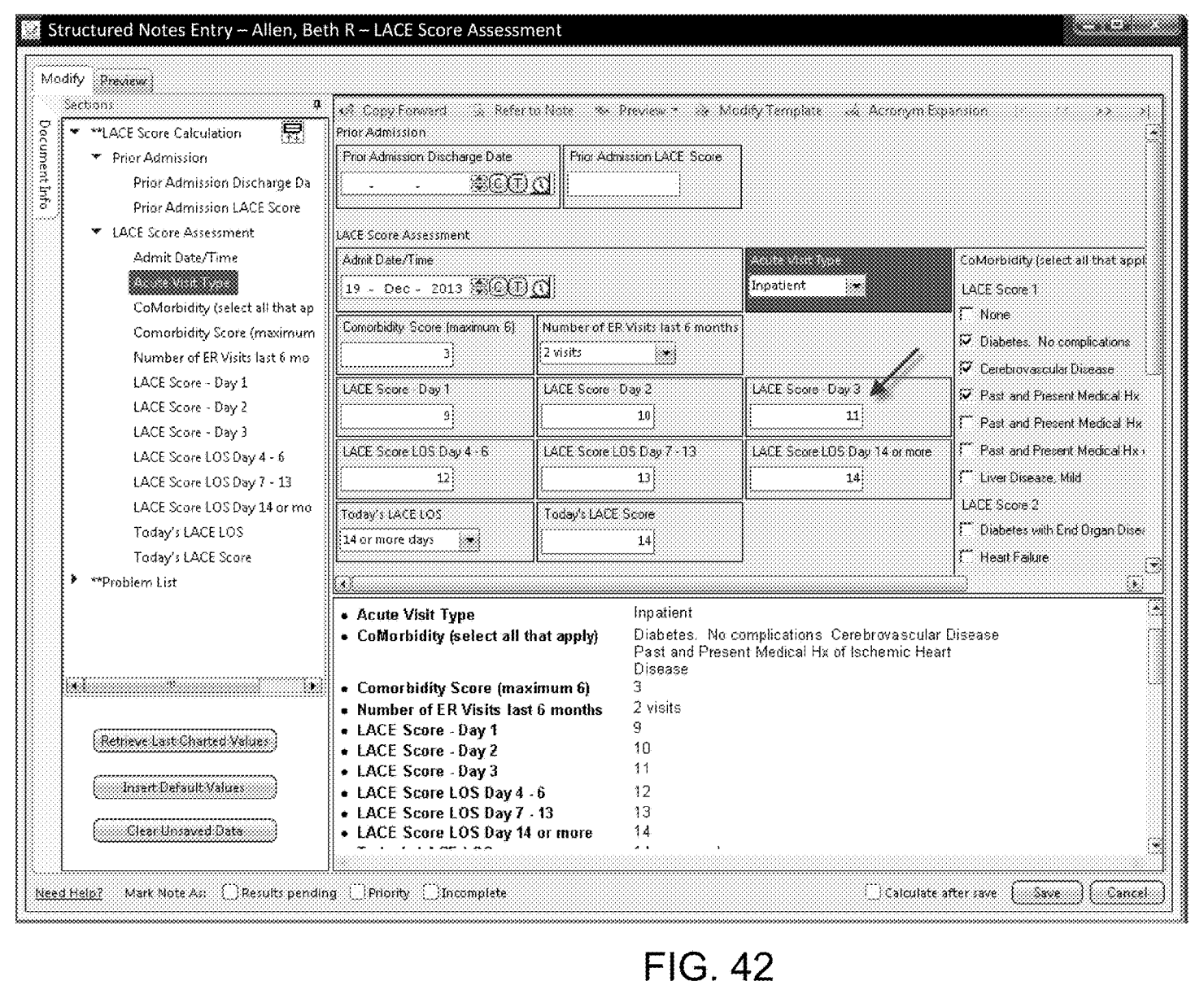

FIG. 42 illustrates just the "Structured Notes Entry" user interface window of FIG. 41 for clarity.

FIGS. 43-48 each illustrates an exemplary sequence of representative steps performed in the exemplary EHR software for joining data in different respective contexts.

Figure 1:
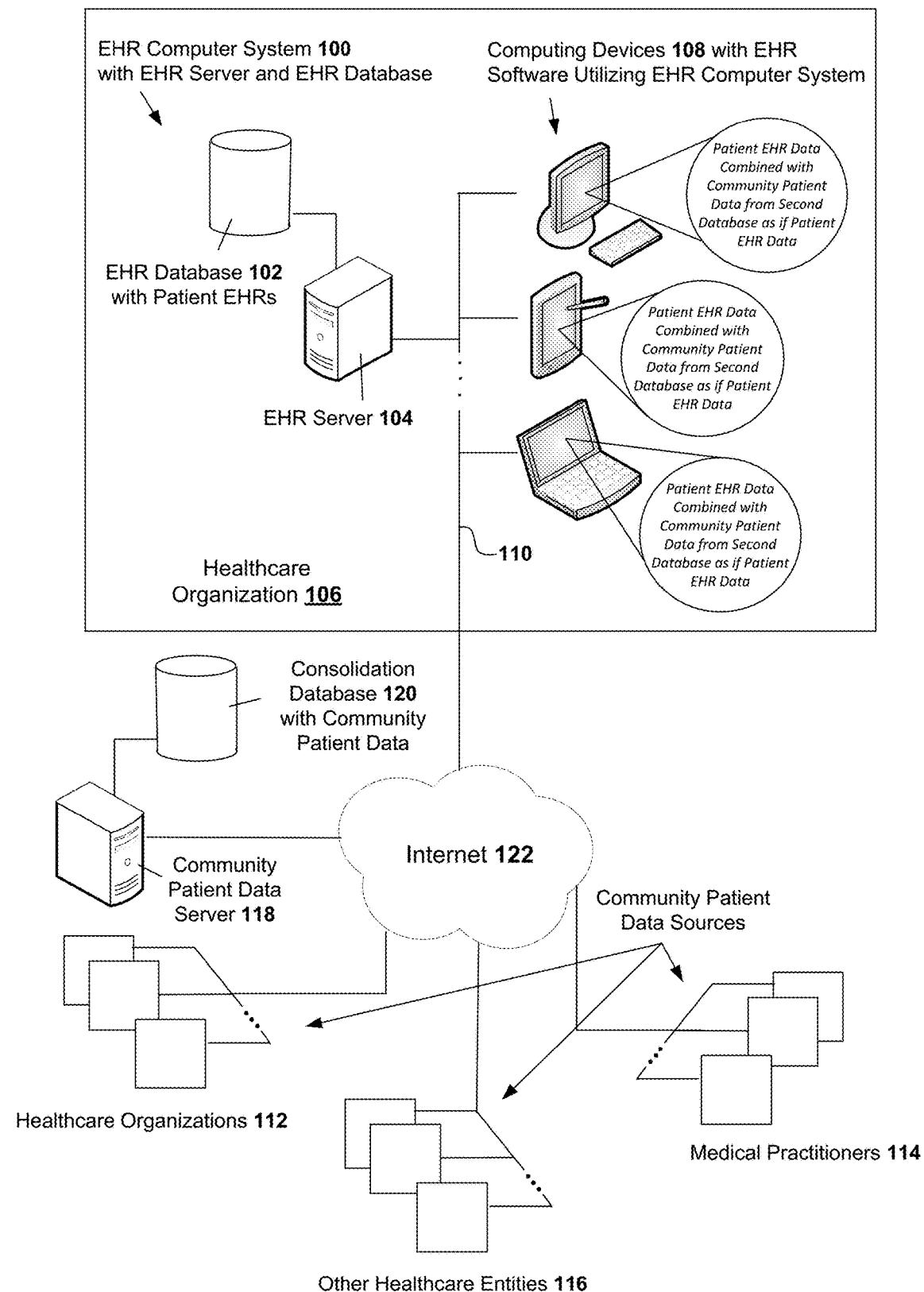
FIG. 1 illustrates an exemplary system in which one or more embodiments of one or more aspects and features of the present invention are intended to be utilized.

Screenshots of additional EHR software implementing one or more aspects and features of the present invention are further disclosed in the Appendix, which is incorporated herein by reference.

DETAILED DESCRIPTION

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Additionally, as used herein, "EHR" is intended to be synonymous with electronic medical record or "EMR"; and "actionable" data when referring to community patient data is intended to mean data that can be utilized by workflows and other logic of EHR software as if the community patient data were native EHR data within the EHR computer system of the EHR software.

Referring now to the drawings, one or more preferred embodiments of the present invention are next described. The following description of one or more preferred embodiments is merely exemplary in nature and is in no way intended to limit the invention, its implementations, or uses.

Turning now to the drawings, FIG. 1 illustrates an exemplary system in which one or more embodiments of one or more aspects and features of the present invention are intended to be utilized. In particular, in FIG. 1 an electronic healthcare record (EHR) Computer System 100 includes one or more EHR databases, represented by EHR Database 102, and one or more EHR servers for accessing the databases, represented by EHR server 104. EHRs are maintained in the EHR database 102 by a first party (shown, for example, as being a healthcare organization 106) for a plurality of patients.

The healthcare organization 106 may comprise, for example, one or more hospitals and associated medical practitioners, all of whom utilize the same EHR Computer System 100 for their patients. The healthcare organization 106 in FIG. 1 alternatively may represent a medical practice, at which all of the healthcare providers in the practice use the same EHR Computer System 100.

FIG. 1 further includes a plurality of computing devices 108, each including a processor and non-transient computer-readable medium having EHR software that utilizes the EHR Computer System 100 by communicating over a computer network 110. The computing devices 108 may comprise, for example, desktop computer, tablets, laptops, and smartphones. In some embodiments, at least some of the computing device 108 comprise iPads. Communications over the computer network 110 by some of the computing devices 108 may include wireless communications at the computing devices. The computer network 110 may comprise, for example, a LAN, a VPN, or combination thereof, wherein the computing devices 108 communicate with the EHR server 104 using, for example, TCP/IP over Ethernet.

The EHR software provides one or more user interfaces for view on display screens operably connected to the computing devices, through which user interfaces healthcare providers using the computing devices 108 can access, view, update, and create healthcare data for a patient, and save such data in a respective EHR of the patient in the EHR Database 102.

Having current and complete healthcare information about a patient when providing healthcare services to the patient is important. Healthcare information about a patient maintained in the EHR Database 102 in fact may be incomplete, as other hospitals or medical practitioners may have provided healthcare services to a patient, the data regarding which would be in the particular EHR database used in the EHR system of such other hospitals or medical practitioners. Such other sources of healthcare information about the patient is represented in FIG. 1 by the "Community Patient Data Sources", which include, for example, healthcare organizations 112, medical practitioners 114, and other healthcare entities 116 that are different from those constituting at least part of the Healthcare Organization 106 and using EHR Computer System 100.

In accordance with preferred embodiments of the invention, healthcare information about patients is retrieved from the Community Patient Data Sources by one or more servers, represented in FIG. 1 by community patient data server 118, and consolidated in Consolidation Database 120 that is operably connected to community patient data server 118. The data is communicated over the Internet 122 from the community patient data sources to the community patient data server 118.

The server 118 and Database 120 may be maintained by a party different from Healthcare Organization 106, and different from each of the healthcare organizations 112, medical practitioners 114, and other healthcare entities 116. However, it is contemplated that such party that maintains server 118 and Database 120 may in fact be, or be related through corporate structure to, Healthcare Organization 106 or one or more of the healthcare organizations 112, medical practitioners 114, and other healthcare entities 116. Moreover, such party may comprise a governmental agency or department and may not be a privately or publicly held legal entity. As sometimes used herein and/or in the incorporated references, "dbMotion" refers to such a company that maintains and provides such a server and database.

In any such scenario, it will be appreciated that the Database 120 is separate and different from EHR Database 102 and the data structures, including fields and properties thereof, may—and probably in practice will—be different at least to some extent. For example. The Database 120 may save patient community data in a universal record data structure according to a predefined industry schema, whereas the EHR Database 102 may save patient data in a proprietary record data structure for which field mappings may be required when transferring or importing patient community data from Database 120 into the EHR Database 102.

In addition to running the EHR software, each of the computing devices 108 preferably runs software by which the computing device 108 communicates with server 118 and retrieves patient community data from Database 120. Such communications preferably occur over the Internet 122. In an alternative implementation, a proxy server may be used to communication between the server 118 and the computing devices 108.

Figure 1A:
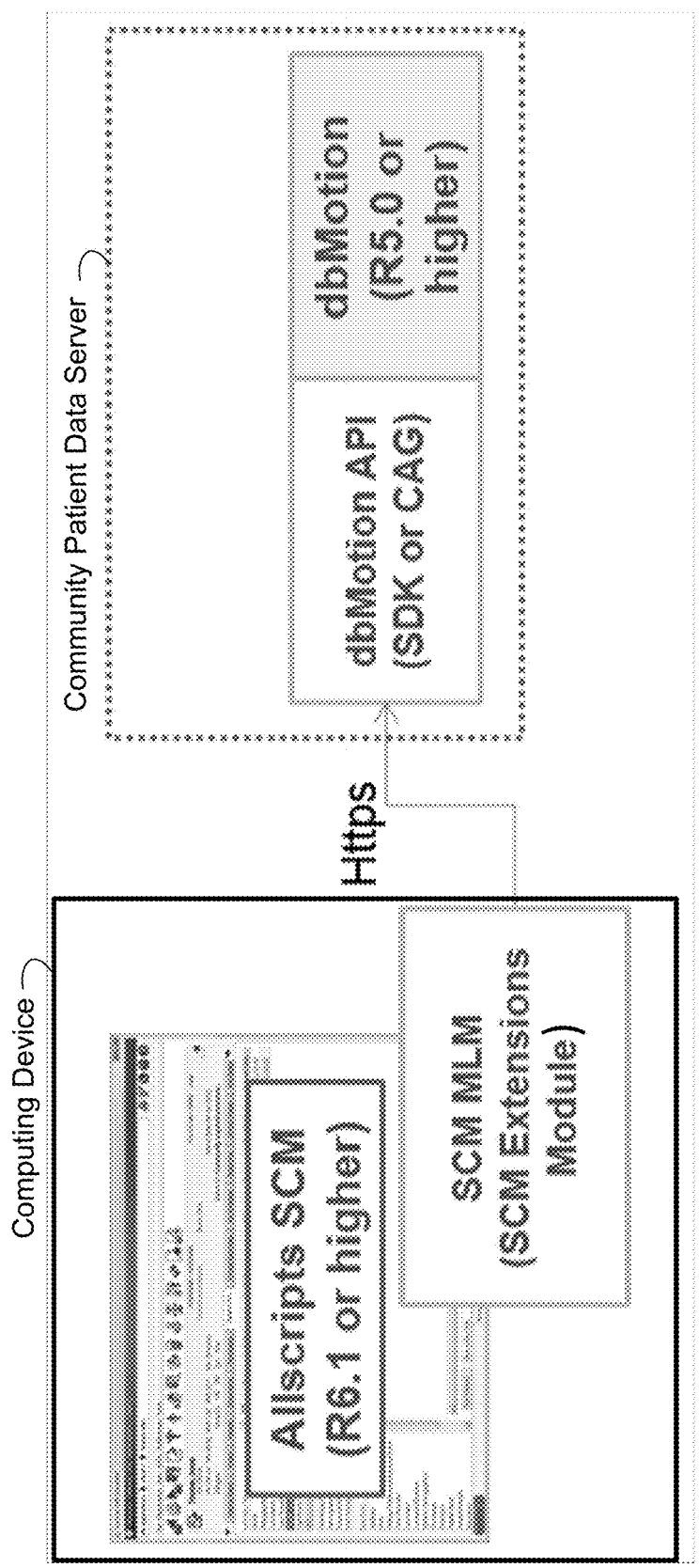
FIG. 1A illustrates a high level architectural illustration of communications between a server and a plurality of computing devices.

FIG. 1A illustrates a high level architectural illustration of communications between the server 118 and the computing devices 108. As illustrated in FIG. 1A, the exemplary computing device represented therein runs EHR software commercially available from Allscripts Healthcare Solutions, Inc., or one of its affiliates or subsidiaries. The exemplary EHR software in FIG. 1A is sold under the trademark "Sunrise Clinical Manager" and is sometimes referred to as "SCM" (and also is known as "Acute Care EHR"). An extension software module is shown, which communicates via https with dbMotion software for obtaining community patient data from a dbMotion server and dbMotion database in which community patient data is maintained, said server and database corresponding to server 118 and Database 120 in FIG. 1A.

Such extension software module may represent, for example, medical logic modules (MLMs) and DLLs, which enable installation specific configurations and customized processes to integrated into the operation of SCM at any particular installation. The computer source code included herewith and forming a part hereof includes such modules and libraries, as well as further optional enhanced/altered base SCM code extending the capabilities of the EHR software in making use—and taking advantage of—the joined actionable community data, including in documentation and structure note creation. Indeed, it is believed that the computer source code provides a commercial ERH solution unlike any other with respect to the ease with which semantically organized and actionable community data is provided inside of the EHR—and within workflows—to the benefit and use by a healthcare provider. Exemplary, representative steps embodying this are illustrated in FIGS. 43-48. Each of these figures illustrates an exemplary sequence of representative steps performed in the exemplary EHR software for joining data in different respective contexts.

Specifically, FIG. 43 illustrates an exemplary sequence of representative steps performed in the exemplary EHR software for joining data in the context of allergies and registering an event handler for interjecting the joined data when screening for allergies for a patient with the EHR software.

FIG. 44 illustrates an exemplary sequence of representative steps performed in the exemplary EHR software for joining data regarding "home" medications taken by a patient and registering an event handler for interjecting the joined data when performing, for example, order reconciliation for a patient with the EHR software.

FIG. 45 illustrates an exemplary sequence of representative steps performed in the exemplary EHR software for joining data regarding health issues of a patient and registering an event handler for interjecting the joined data when performing, for example, noting or documentation for the patient with the EHR software.

FIG. 46 illustrates an exemplary sequence of representative steps performed in the exemplary EHR software for joining data regarding allergies and existing orders and registering an event handler for interjecting the joined data when checking for conflicts and generating alerts within the EHR software.

FIG. 47 illustrates an exemplary sequence of representative steps performed in the exemplary EHR software for joining document data for a patient and registering an event handler for interjecting the joined data when loading the documents tab for a patient within the EHR software.

FIG. 48 illustrates an exemplary sequence of representative steps performed in the exemplary EHR software for joining data regarding patient data for a plurality of patients, e.g., a population of patients, and registering an event handler for interjecting the joined data when presenting a population health view or views, e.g., population health widgets or tiles, within the EHR software.

In accordance with one or more aspects and features of the present invention, and referring again to FIG. 1, EHR software running on each of the computing devices 108 retrieves EHR data for one or more patients for presentation to a healthcare provider using the respective computing device. The EHR data also preferably is utilized in workflows and other logical processing at the computing device for assisting in clinical decision making by the healthcare provider. This preferably includes, for example, providing such support at the point-of-care associated with an encounter with the patient for which the EHR data is retrieved from the EHR database for use by the EHR software running at the computing device. In addition to the EHR data, patient community data additionally is retrieved for the same patient or patients for which the EHR data is retrieved. As shown in FIG. 1, the community patient data is combined with the EHR data, and the community patient data is presented to the healthcare provider at the computing device as if the community patient data were EHR data for the patient. This is done without importing the community patient data into the EHR Computer System, i.e., without saving the community patient data in the EHR Database 102. This is not to suggest that community patient data cannot or is not imported and saved in the EHR Database 102, but that such steps are not required for performance of one or more embodiments of the present invention.

Moreover, the joined or combined data for the patient furthermore is utilized in workflows and other logical processing of the EHR software as if it were EHR data. The community patient data thus can be consumed in the EHR software. Indeed, in at least some preferred embodiments, the EHR software is unable to identify or distinguish the community patient data joined with the EHR data; the community patient data appears and is handled by the EHR software in such preferred embodiments as if such community patient data had already been imported into the EHR database and had was retrieved when the EHR data was retrieved from the EHR Database 102, when in fact the community patient data may not have been imported into the EHR Database 102. In other embodiments, the EHR software may be modified to facilitate or enhance the joining of the data and operations based thereon, again without importing the community patient data into the EHR of the patient; without saving the community patient data in the EHR database; or both.

While the computing devices each has been describe as a physical device used by a healthcare provider on which the EHR software is installed on that executes the EHR software, such as a laptop, desktop, or tablet for example, in contemplated alternatives the computing device is used by a healthcare provider to interact with and display (i.e., remotely control) a virtual machine instance that is hosted on another computing device, such as a server, on which virtual machine instance the EHR software is installed and executed. In such situations the computing device may be a thin client. In this scenario, the user interface still is provided for display on—and interaction with the healthcare provider at—the computing device itself, and at least in a broad sense, the EHR software still is run by the user via the computing device even though the processor of the remote server physically executes the EHR software instructions. At a more technical level of granularity, though, the data retrieval and joining does not occur at the computing device of the healthcare provider (user), but at the remotely located computer or server.

Additionally, it will be appreciated that while an EHR server and EHR database are described herein, the EHR server alternatively may comprise the EHR database, representing a single server that both receives and responds to requests for patient healthcare information and that maintains patient healthcare information in a database.

In yet alternative implementations, a server rather than the computing device joins the EHR data and the community data, and provides the joined data to the computing device of the healthcare provider (user); the data retrieval and joining does not occur at the computing device itself, but at the remote computer or server separately located from the healthcare provider.

The server may be the EHR server. In this respect, medical logic modules may be provided—or other methods of customizations implemented—under which the EHR server, upon receiving a request for healthcare information for a patient, retrieves healthcare information for the patient both from the EHR database and from the community database. Upon receiving the healthcare information from both sources, the data is then joined and provided to the EHR software that is run on the computing device from which is received the request for the patient's healthcare information. Even still, the community information that is retrieved by the EHR server is not imported into the EHR data when joined with the EHR data and provided to the computing device.

Figure 2:
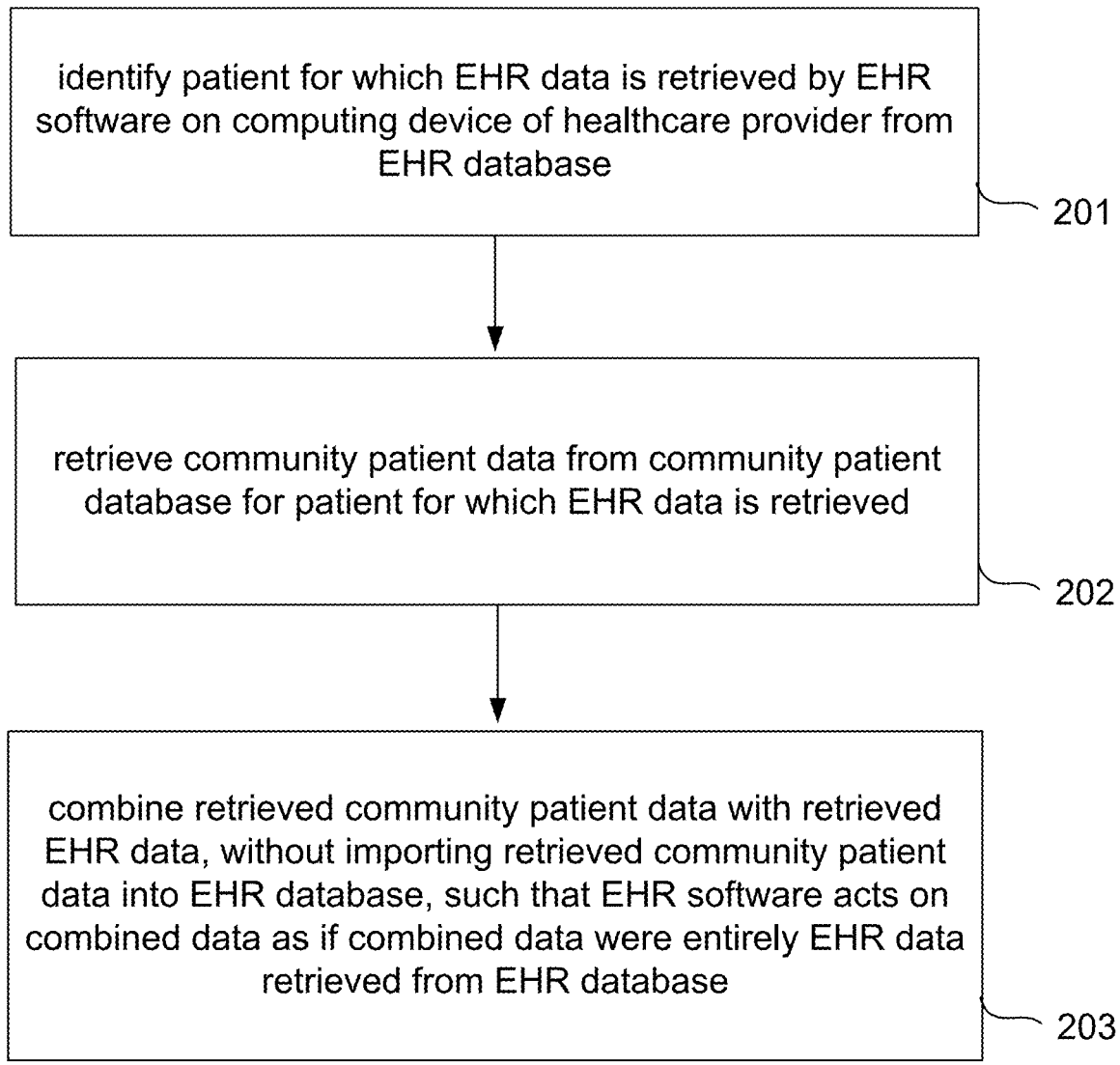
FIG. 2 illustrates a method incorporated in various preferred embodiments of the present invention, which method may be performed within the context of the exemplary system of FIG. 1.

FIG. 2 illustrates a method incorporated in various preferred embodiments of the present invention, which method may be performed within the context of the exemplary system of FIG. 1. In accordance with such method, software—hereinafter referred to as a smart agent—that preferably is separate from the EHR software and also running on a computing device identifies at 201 one or more patients for which EHR data is retrieved from an EHR database by the EHR software. The smart agent at 202 retrieves community patient data from a community patient database for the one or more patients for which the EHR data is retrieved. At 203, the smart agent combines the retrieved community patient data with the retrieved EHR data, without importing the retrieved community patient data into the EHR database, such that the EHR software acts on the combined data as if the combined data were entirely EHR data that was retrieved from the EHR database. The smart agent as described herein is believed to be an improvement, at least in certain respects, to the smart agent implementations disclosed and described in U.S. patent application publication 2012/0215560, incorporated by reference herein.

It will be appreciated that once joined, the community patient data and EHR data appear within the user interfaces of the EHR software. Screenshots of SCM—exemplary EHR software—are shown in FIGS. 3-42, wherein the EHR software utilizes such joined data. References to dbMotion in these drawings represent separate software for so joining community patient data with EHR data in a form that is actionable within—and consumable by—SCM. Furthermore, the exemplary dbMotion software that performs one or more aspects and features of the present invention is operable with EHR software from other third parties and is not limited to use only with SCM, which is used for example only. Is further should be understood that the data is consumed by SCM and presented to users preferably only when such community patient data is applicable given the current SCM context, determined at least in some embodiments based on the user interface selected by and presented to a healthcare provider working in SCM.

With specific regard now to FIG. 3, a user interface is shown in which medication summary information is displayed. The medication summary includes both medication information from the EHR database (six items are listed) as well as medication information not found in the EHR for the patient but found in the community healthcare information for the patient. The community patient data (two items) is presented in the EHR software as if the community patient data had been imported into the EHR for the patient when in this particular case, the community patient data has not been imported. Had community patient data been imported, it would appear as shown in FIG. 3 since the EHR software does not distinguish whether the community patient data is, in fact, imported in to the EHR of the patient.

FIG. 4 illustrates an exemplary alert regarding a duplicate order that has been identified by the EHR software based on joined EHR data and community patient data.

Figure 5:
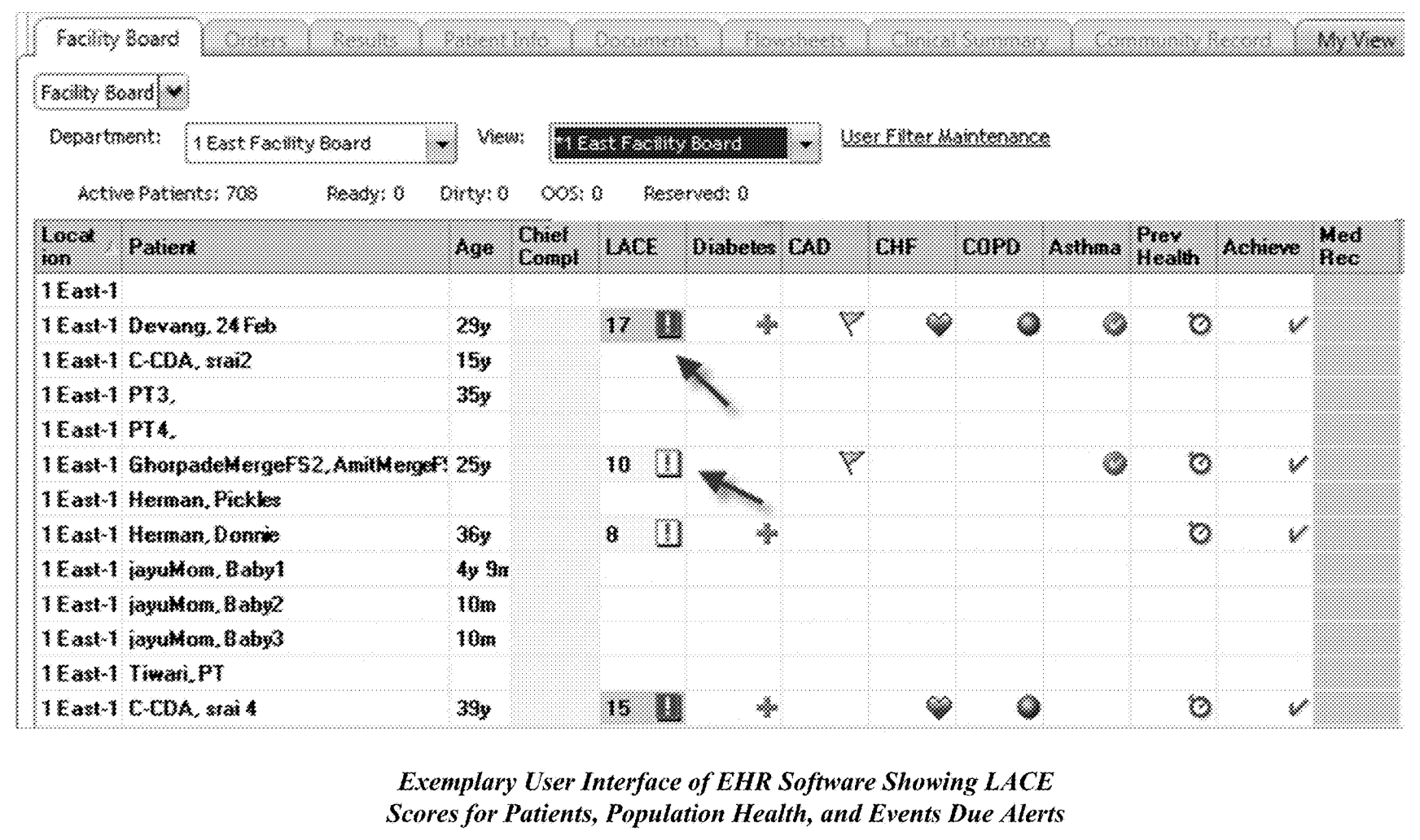

FIG. 5 illustrates a user interface for a "Facility Board" tab in SCM. As shown therein, healthcare information for a number of patients is presented. The healthcare information comprises or is derived from joined EHR data and community patient data, and includes a calculated LACE score based on such joined data; indicators or flags regarding diabetes; indicators or flags regarding CAD; indicators or flags regarding CHF; indicators or flags regarding COPD; indicators or flags regarding Asthma; indicators or flags regarding Prev Health; and indicators or flags regarding "Achieve" (which is described in copending U.S. patent applications of applicant). The healthcare information pertains to patient information as well as population health and events due alerts.

Figure 6:
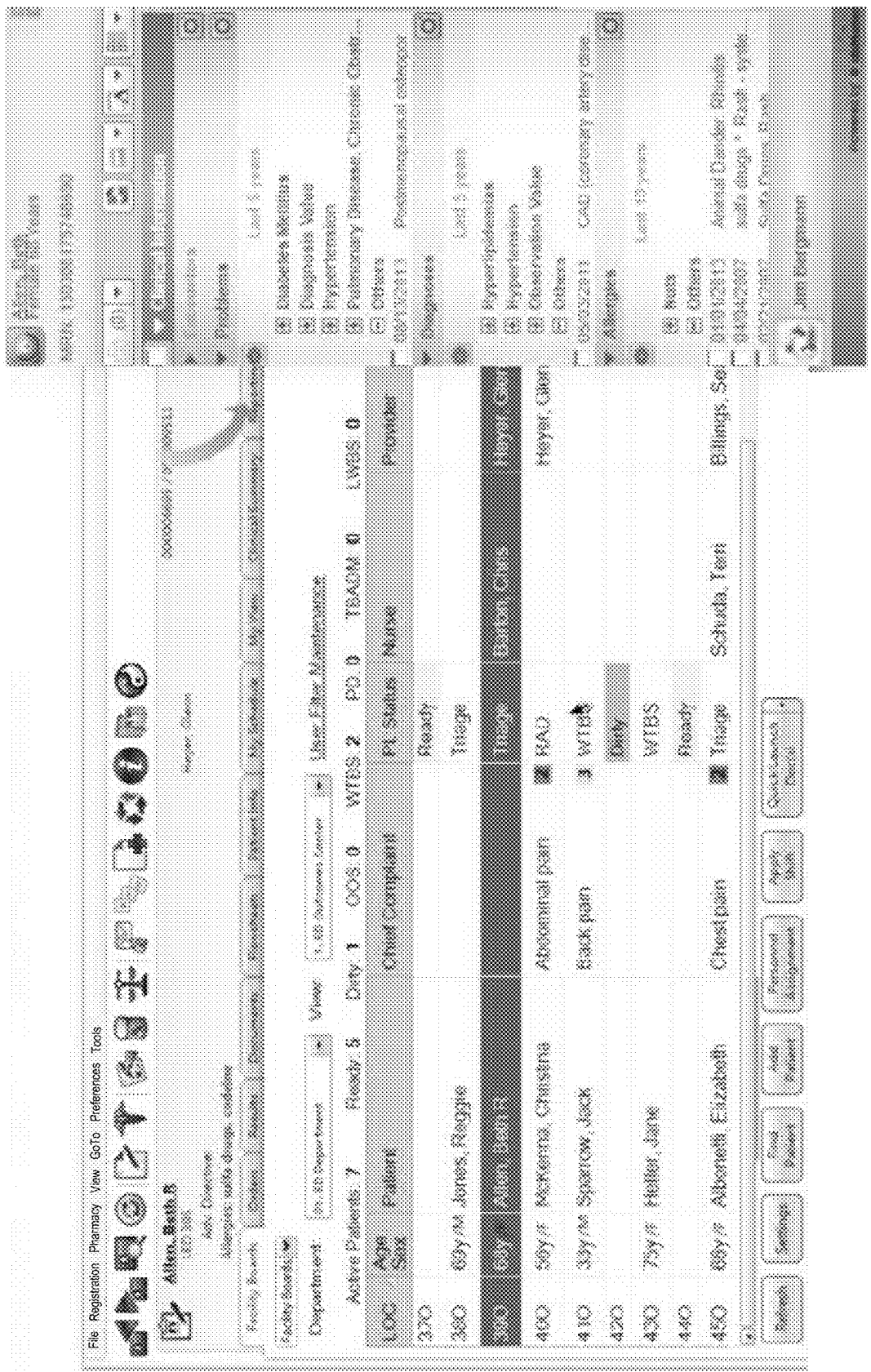
FIG. 6 illustrates another view with more detail of a "Facility Boards" tab of the exemplary EHR software.
Figure 8:
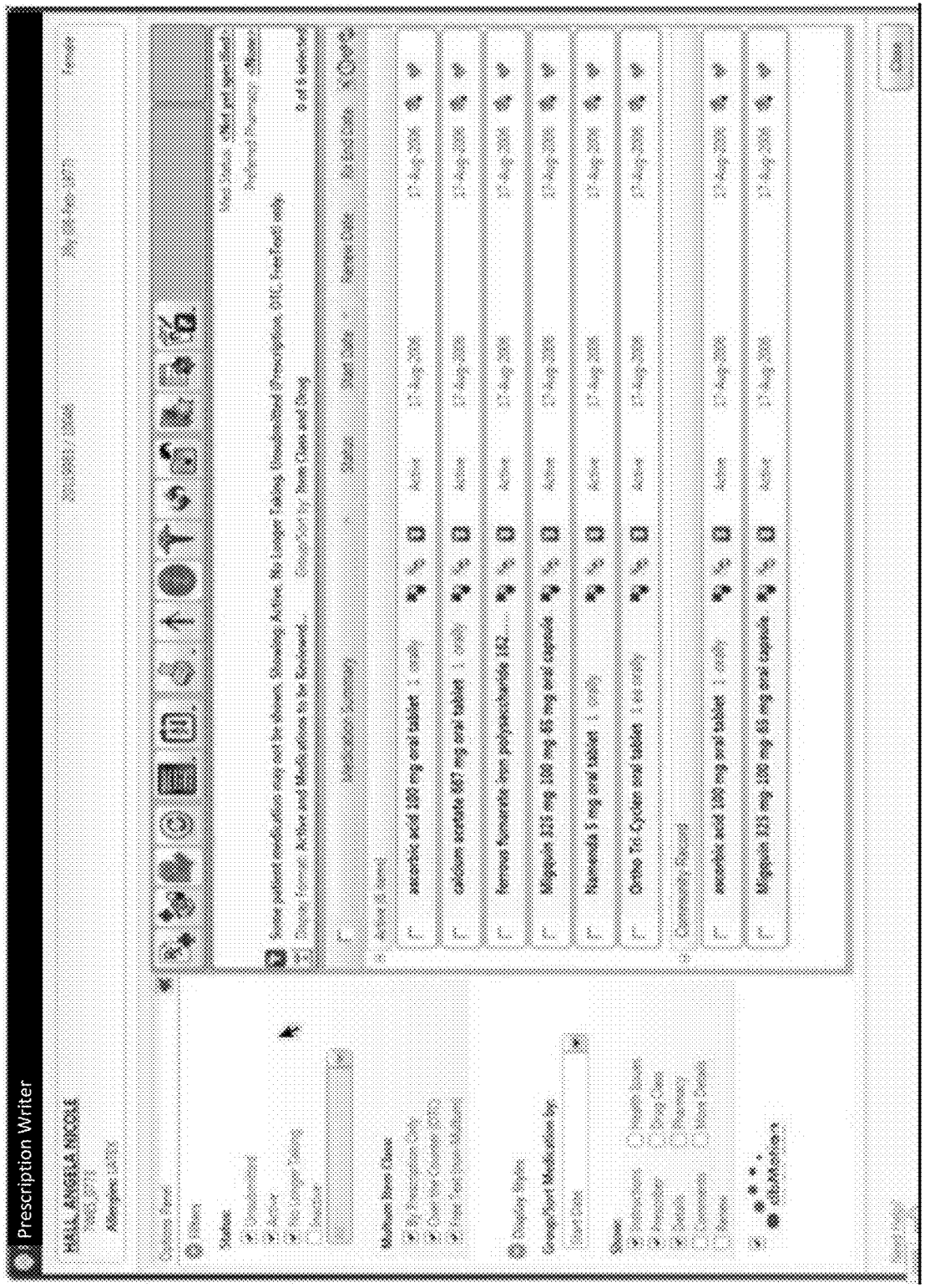
FIG. 8 illustrates a view for a particular patient of an "Prescription Writer" user interface window of the exemplary EHR software.
Figure 9:
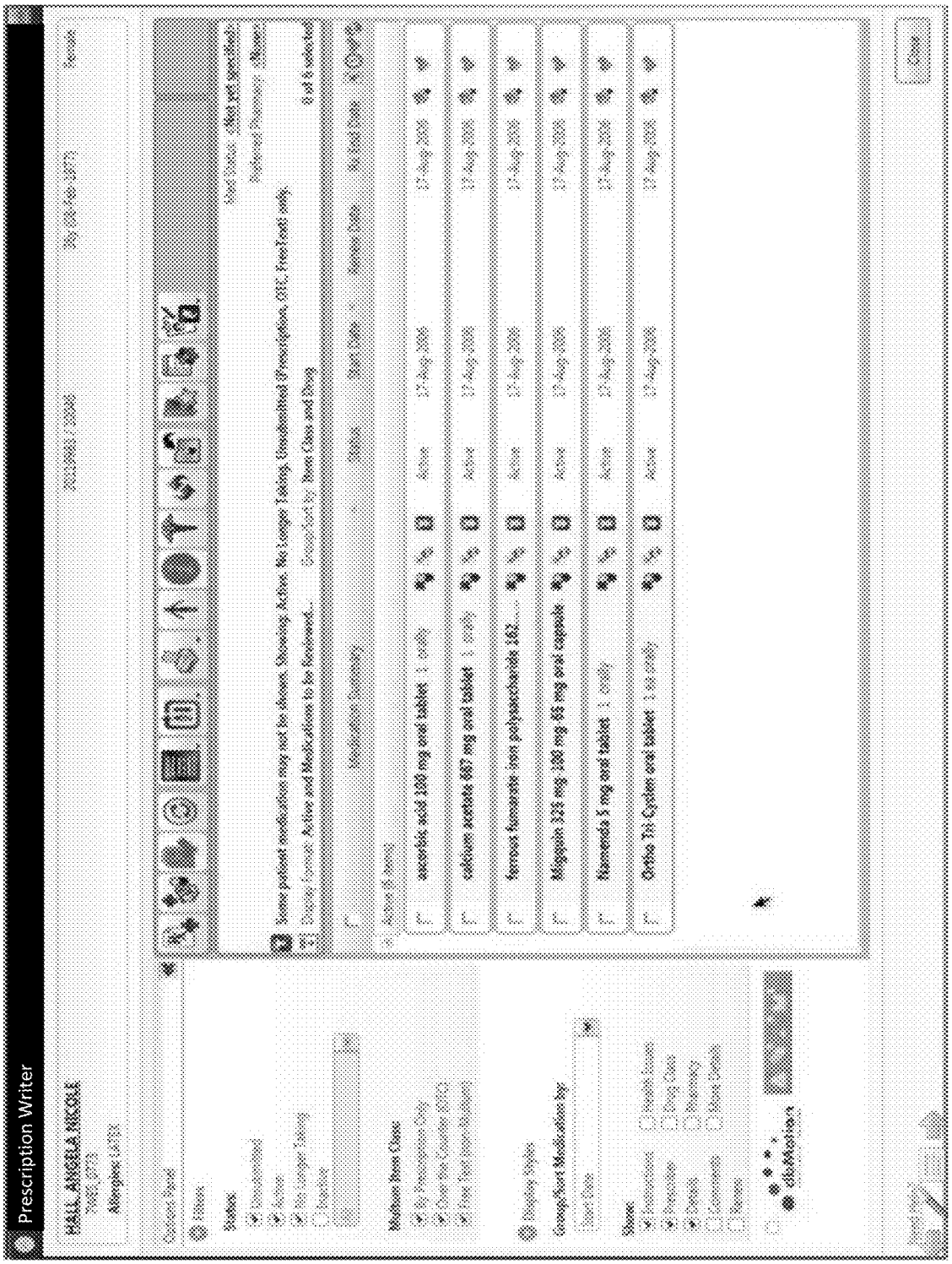
FIG. 9 illustrates another view of the "Prescription Writer" user interface window.
Figure 10:
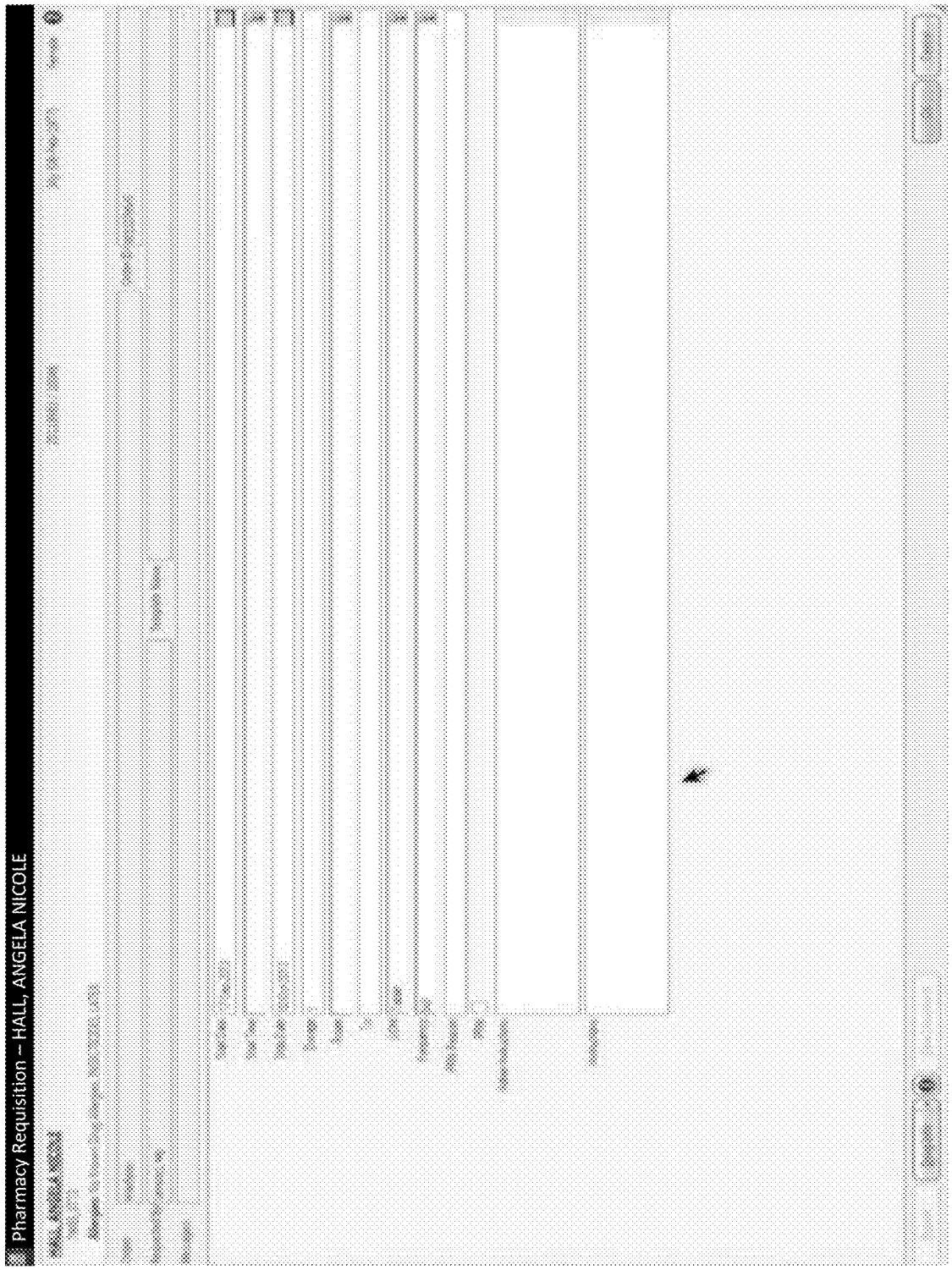
FIG. 10 illustrates a view for a particular patient of an "Pharmacy Requisition" user interface window of the exemplary EHR software.
Figure 11:
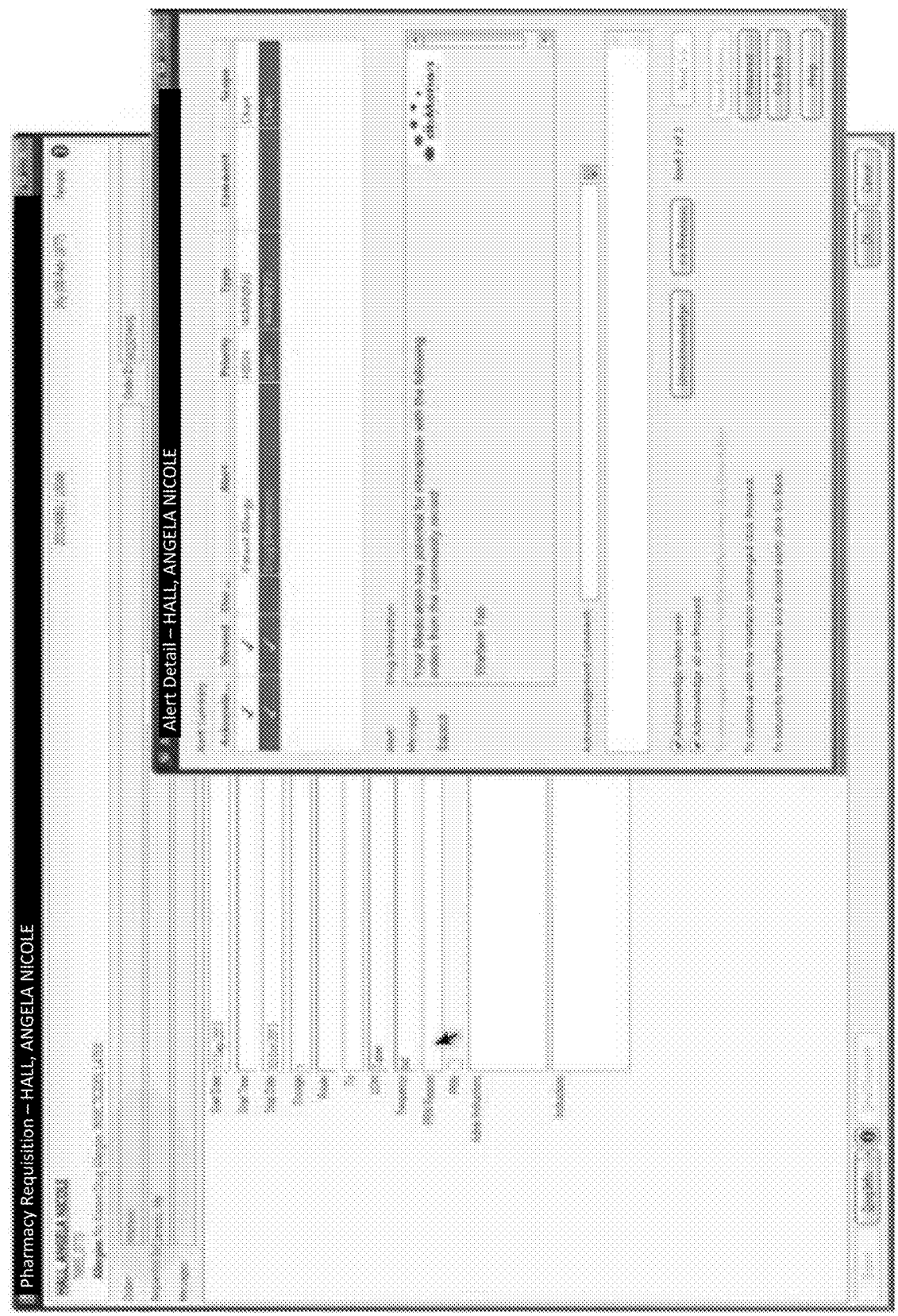
FIG. 11 illustrates an "Alert Detail" user interface window of the exemplary EHR software associated with the user interface window of FIG. 10.
Figure 12:
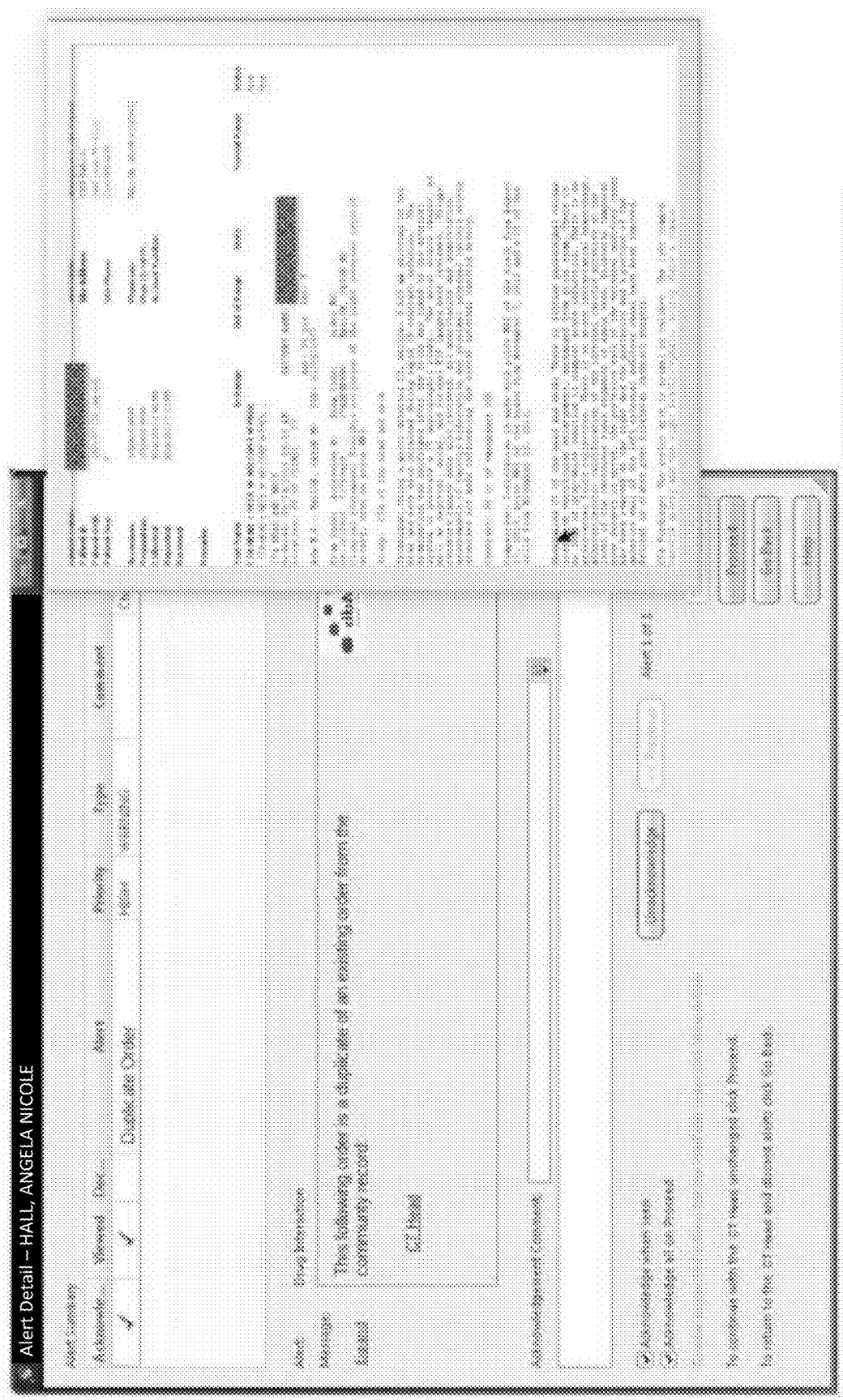
FIG. 12 illustrates an additional user interface window with additional patient information for the patient of the of the user interface window of FIG. 11.
Figure 15:
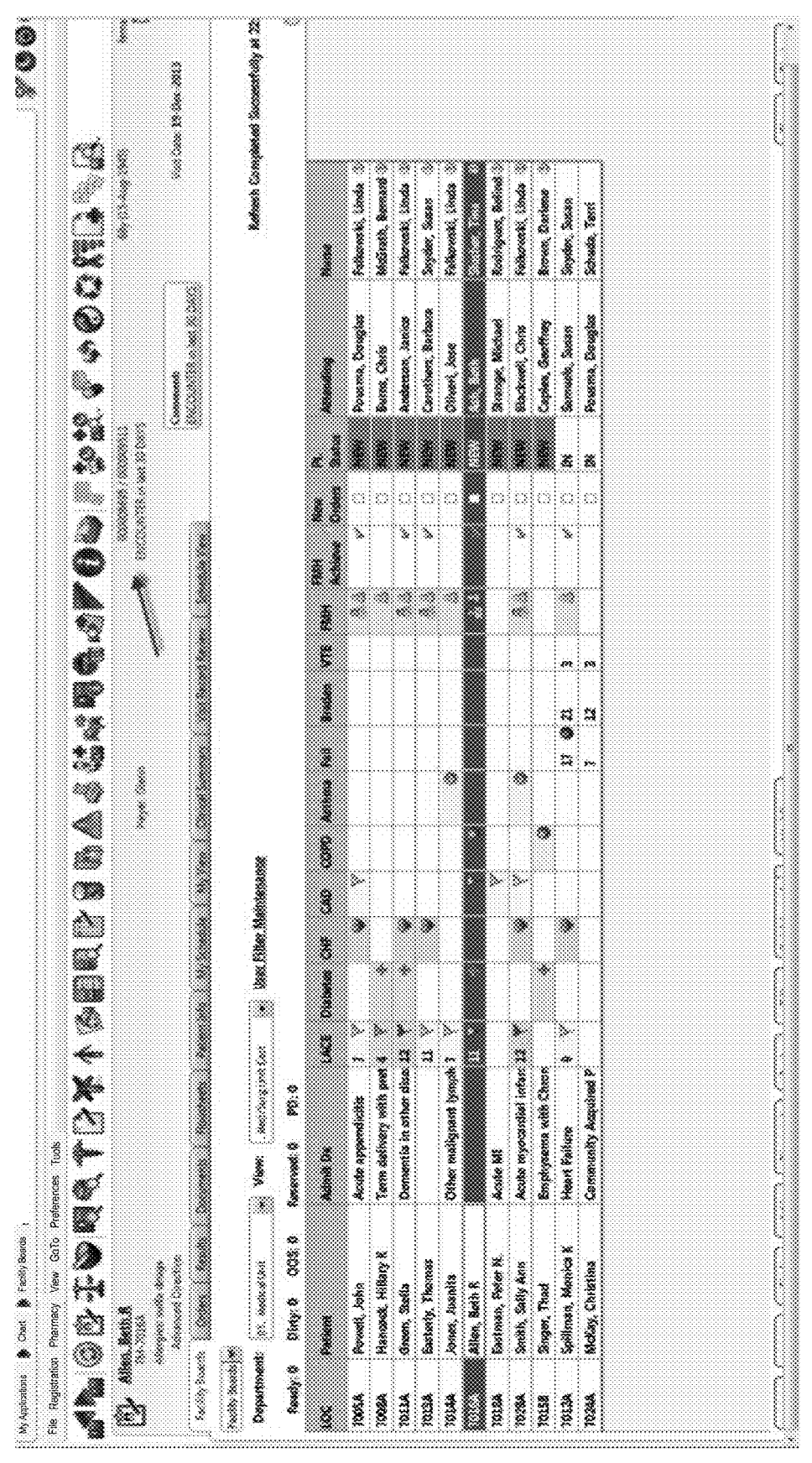
Figure 17:
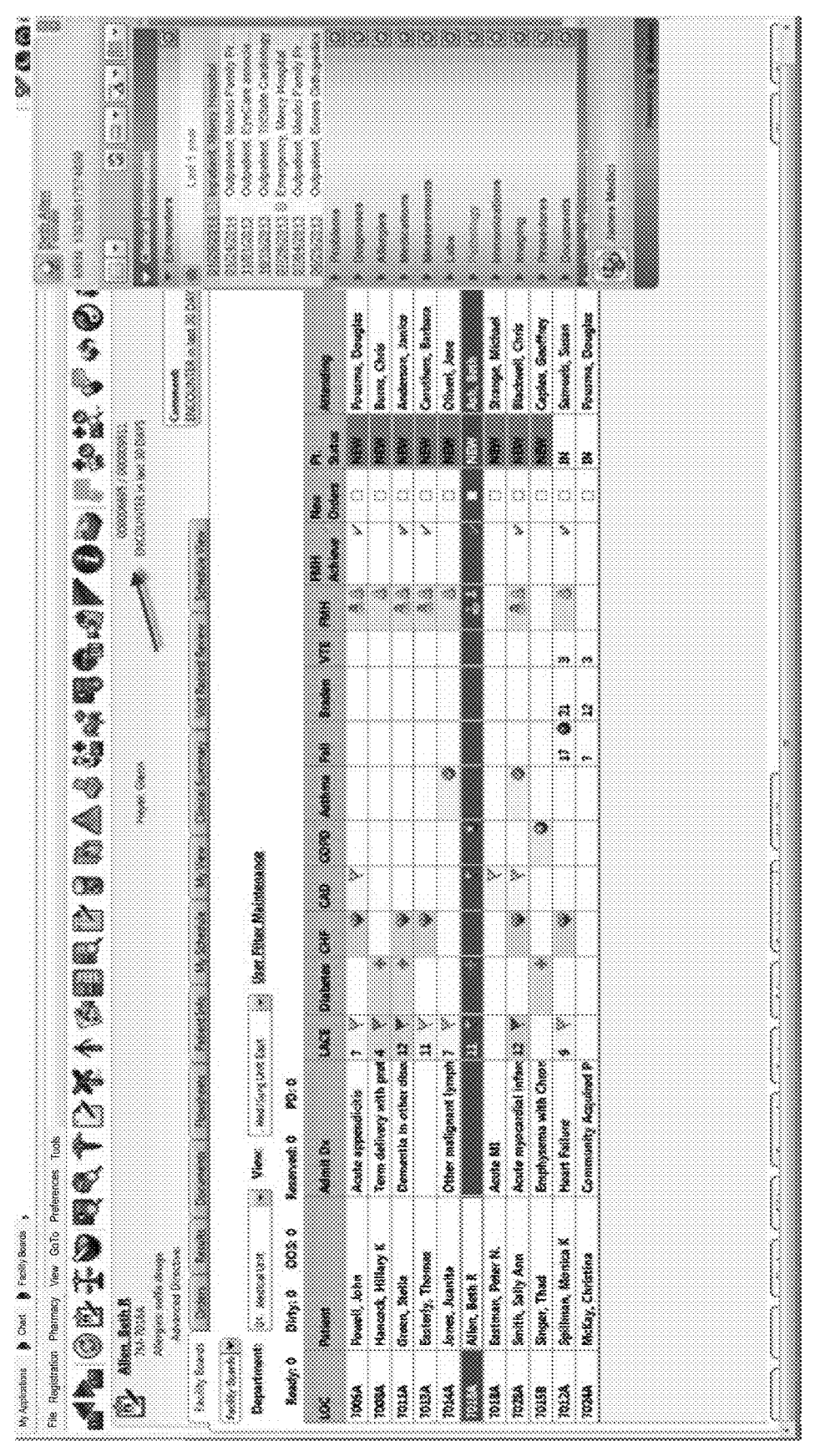
Figure 18:
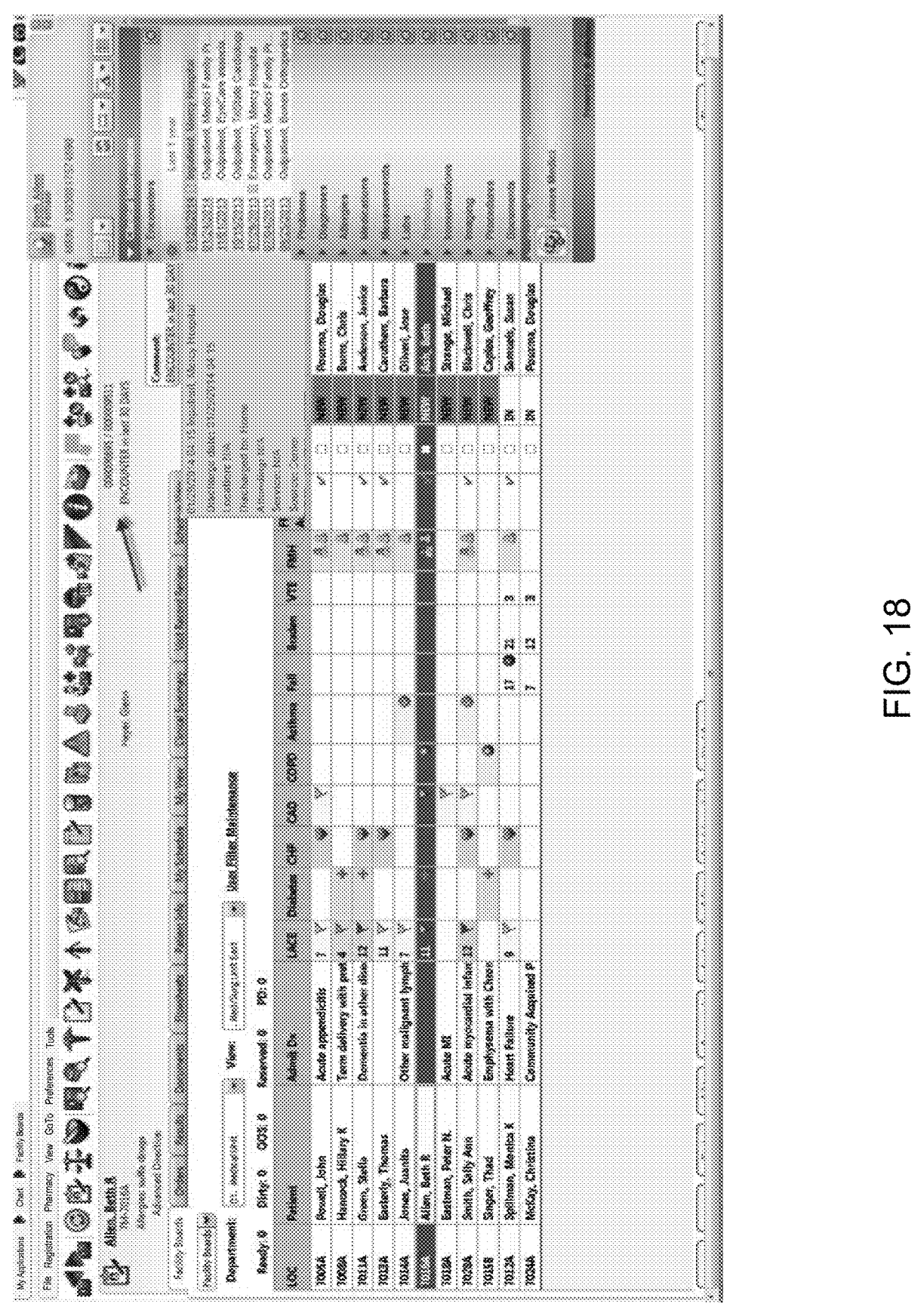
Figure 19:
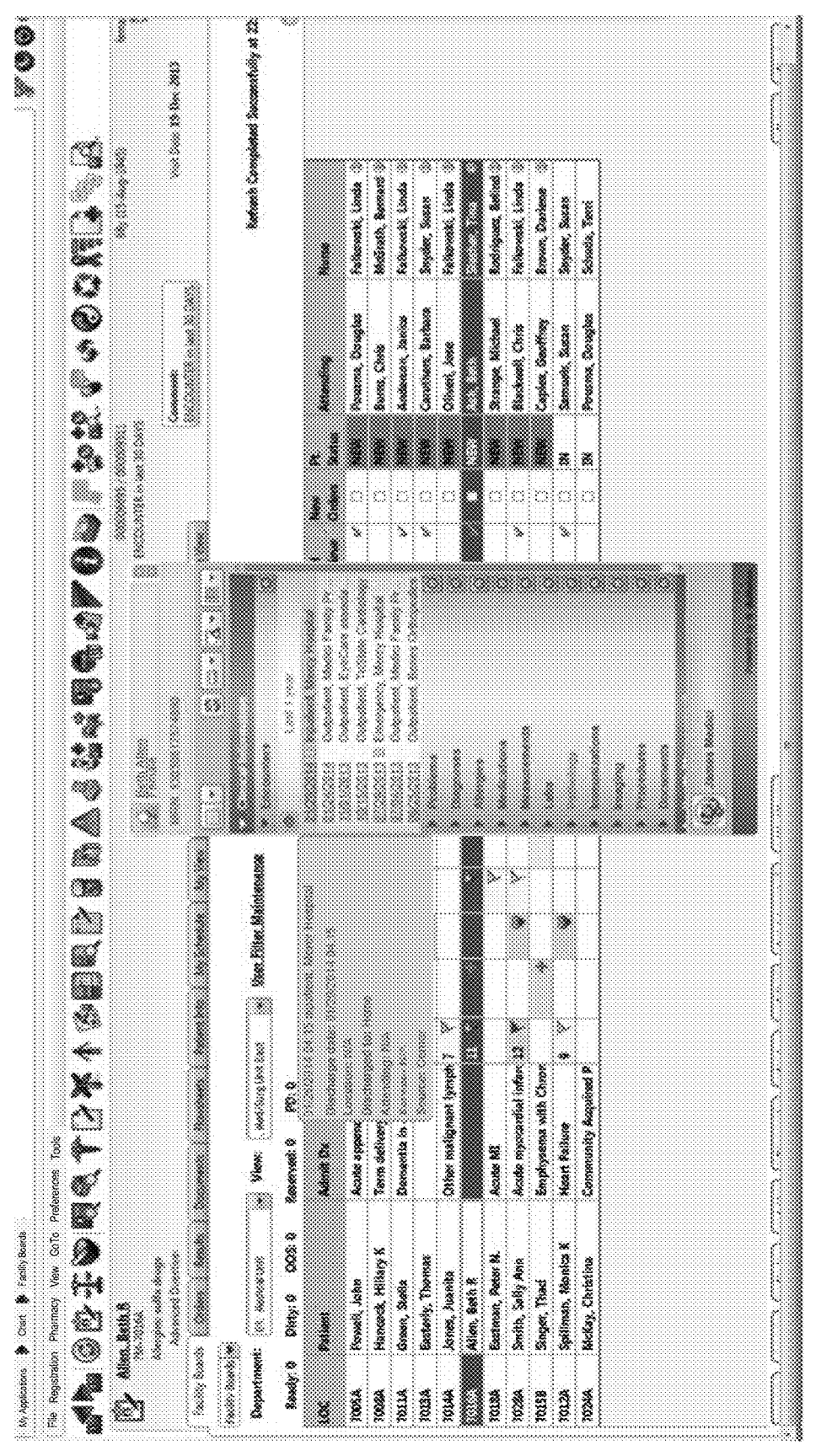

Another view showing more detail of a "Facility Boards" tab of SCM is shown in FIG. 6 and further includes a user interface of the aforementioned smart agent comprising a panel that 'sits' and 'floats' on top of SCM. The smart agent user interface can be minimized and moved around within the display, as represented in FIGS. 16-22. Moreover, FIG. 15 shows a view in which the smart agent interface has been minimized or closed.

Figure 13:
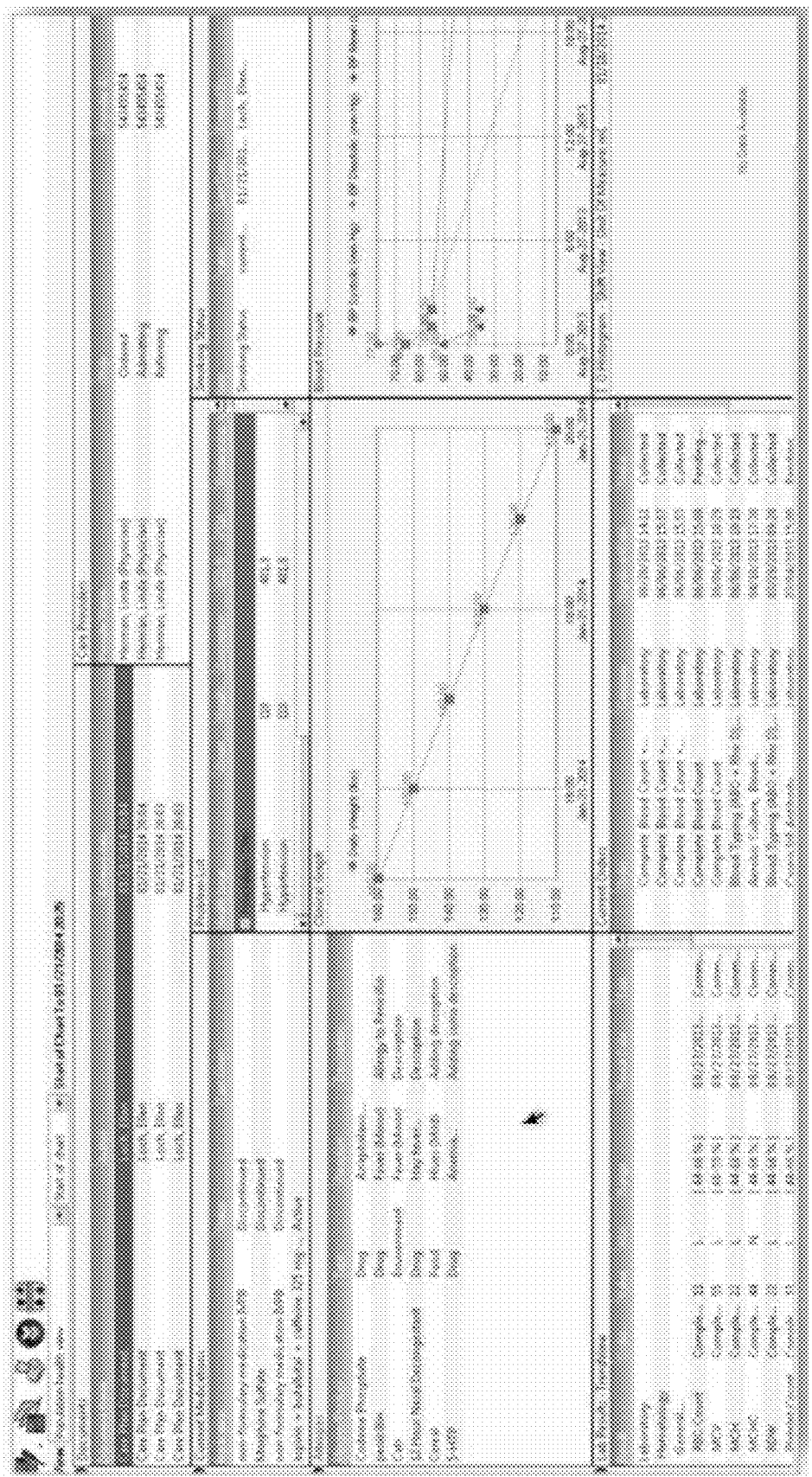
FIG. 13 illustrates a plurality of user interface windows or tiles associated with a population health view of the exemplary EHR software; with respect to population health, joined data can be utilized with results and observations being shown in the various 'information widgets' seen in FIG. 13. It will also be appreciated that the joined EHR data and community patient data can comprise healthcare documents, including PDF documents, such as the documents illustrated in FIGS. 39 and 40.
Figure 16:
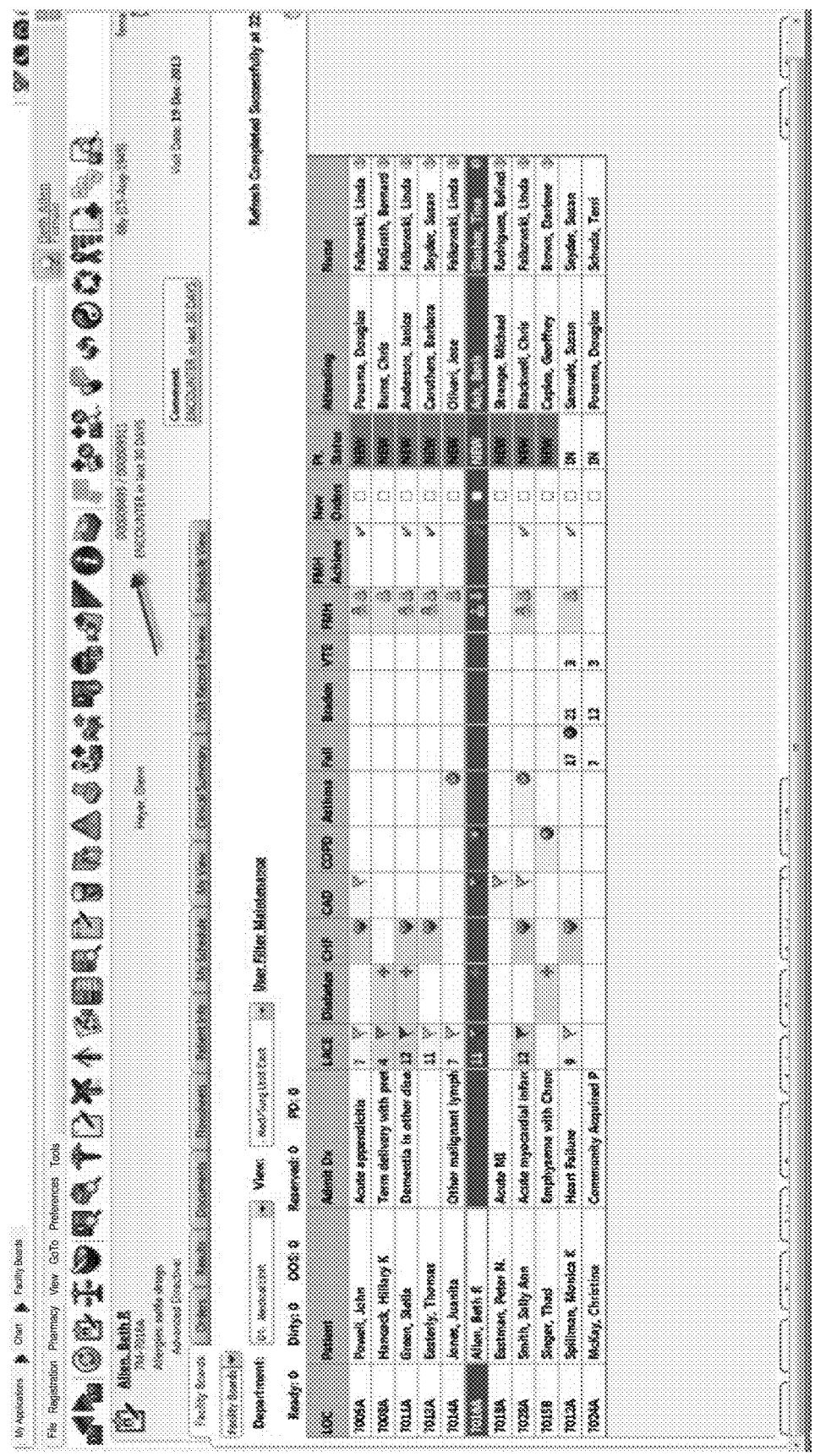
FIG. 16 illustrates a screenshot in which a smart agent user interface is utilized with the user interface window of FIG. 15.
Figure 29:
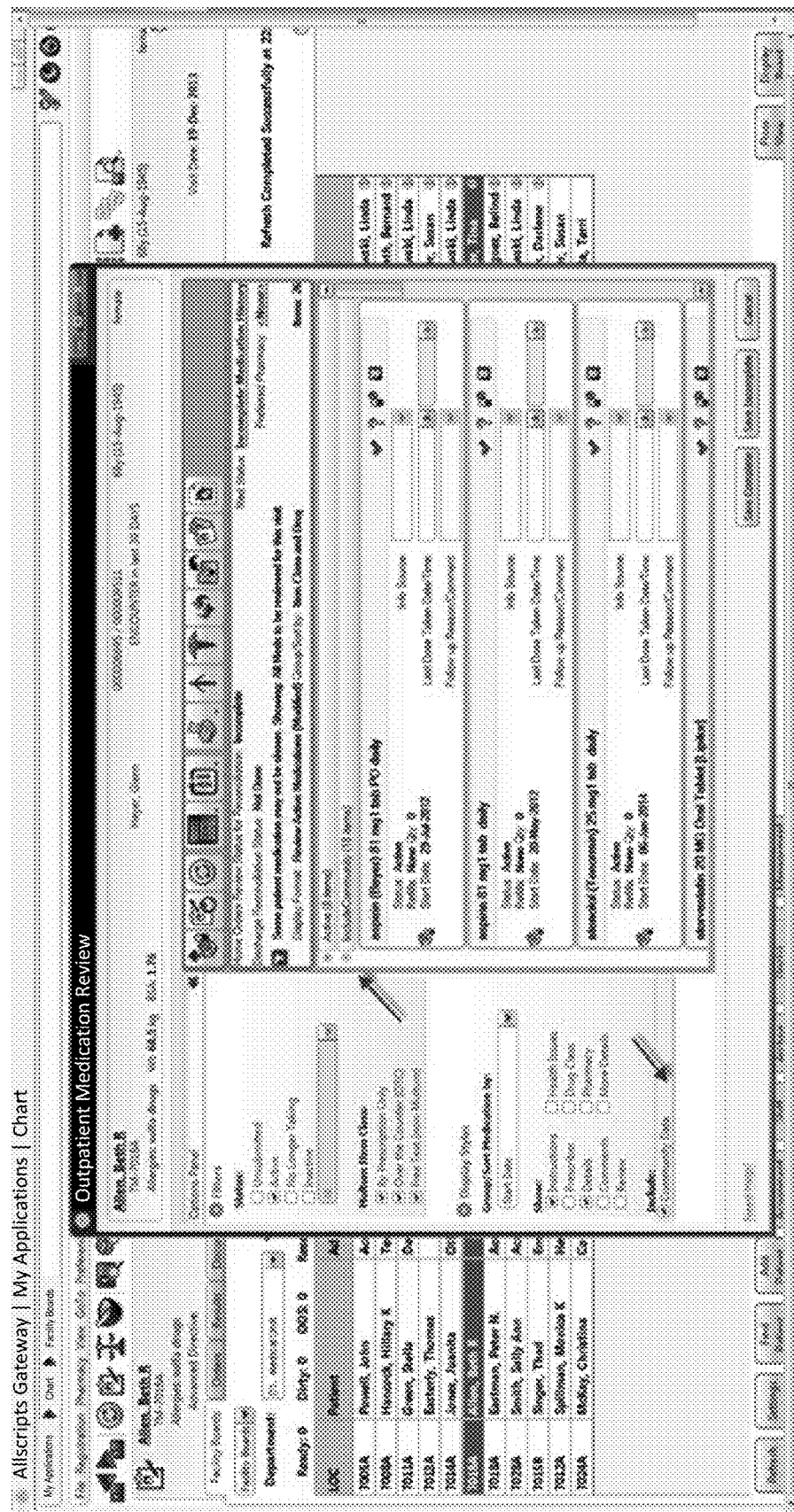
FIG. 29 illustrates an "Outpatient Medication Review" user interface window for the selected patient in the user interface of FIG. 15.
Figure 30:
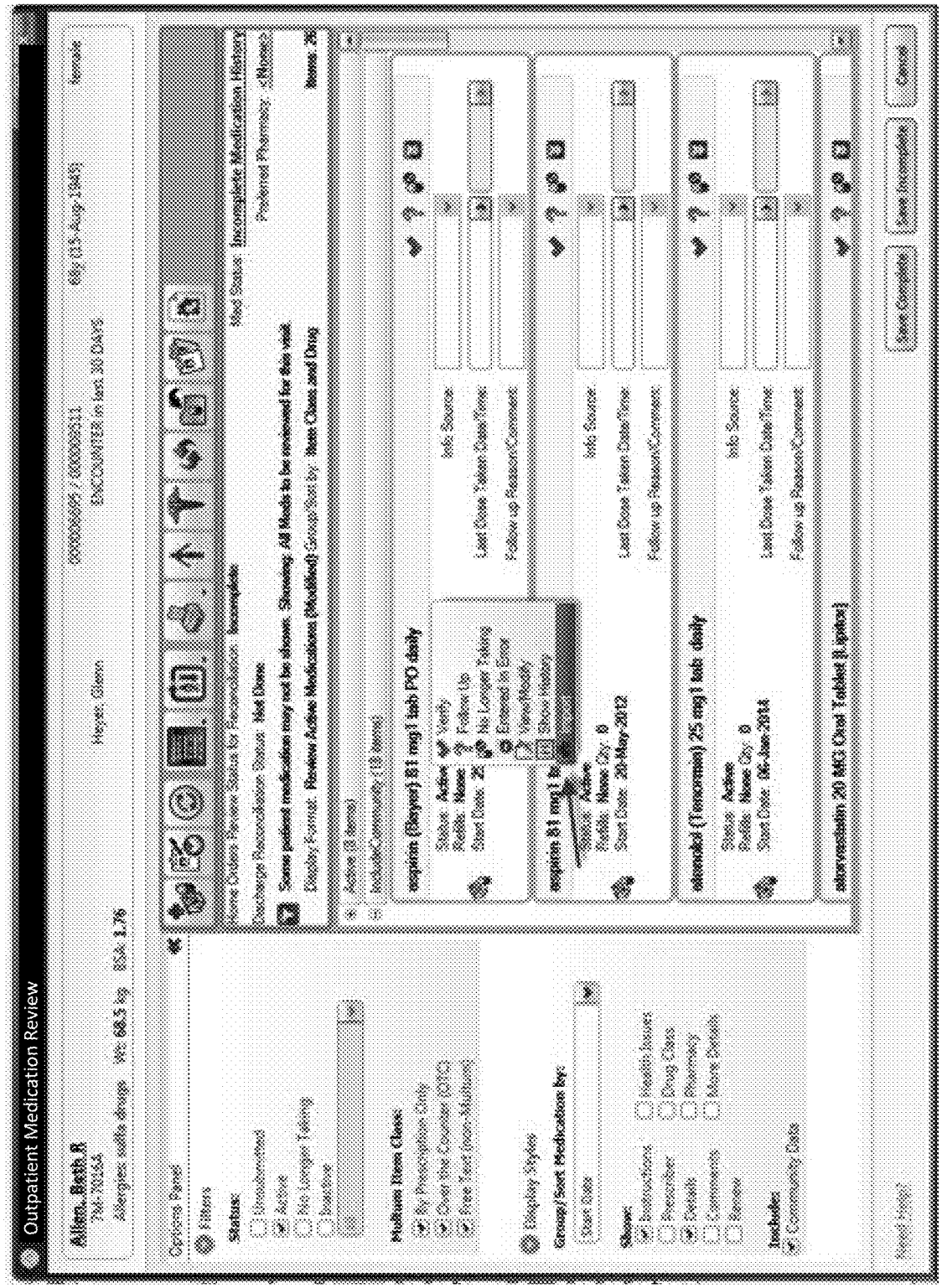
FIG. 30 illustrates the "Outpatient Medication Review" user interface window of FIG. 29, wherein the user interface window of FIG. 15 is omitted for clarity.
Figure 33:
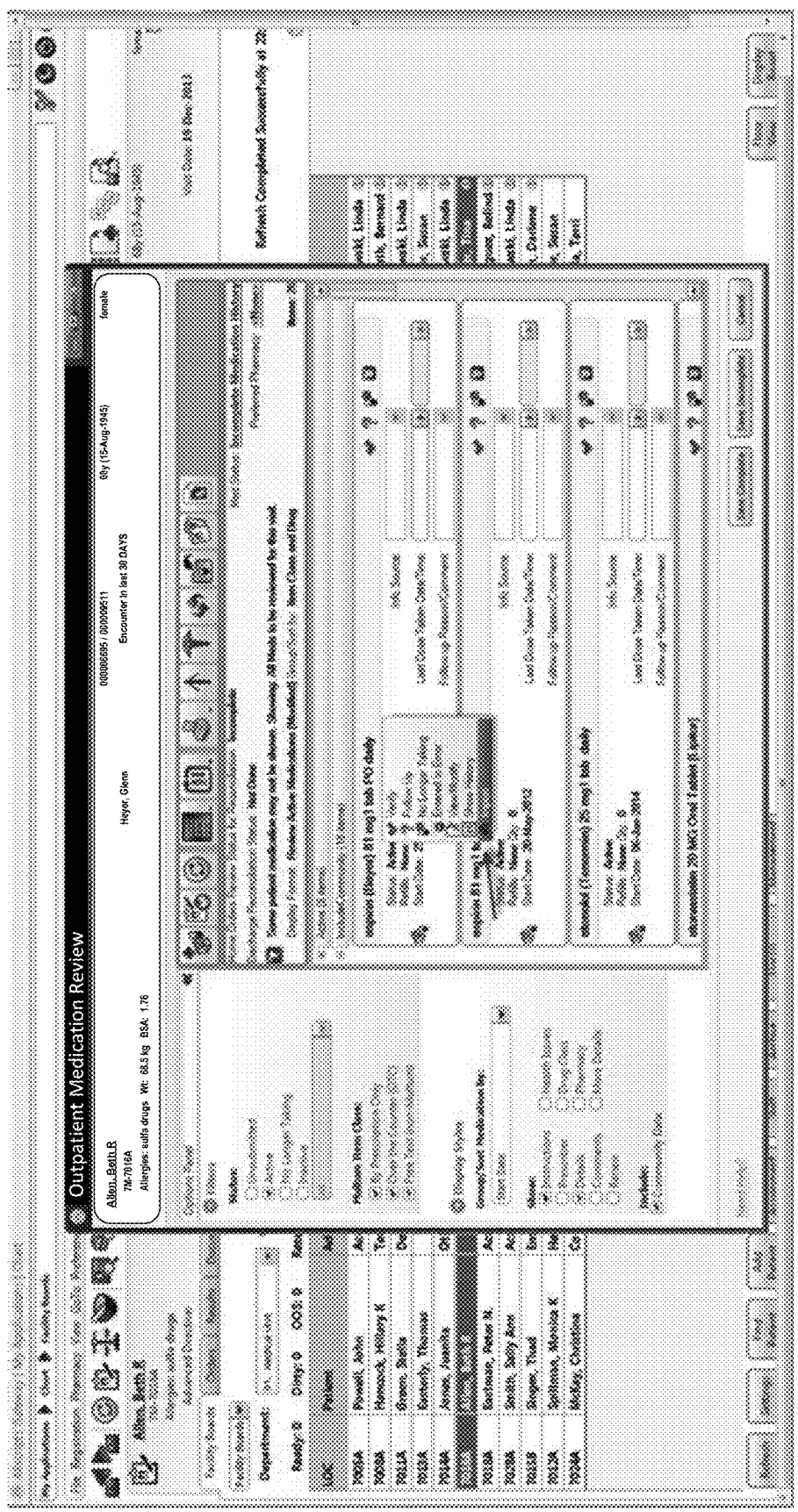
FIG. 33 illustrates another view of the "Outpatient Medication Review" user interface window for the selected patient in the user interface of FIG. 15.
Figure 35:
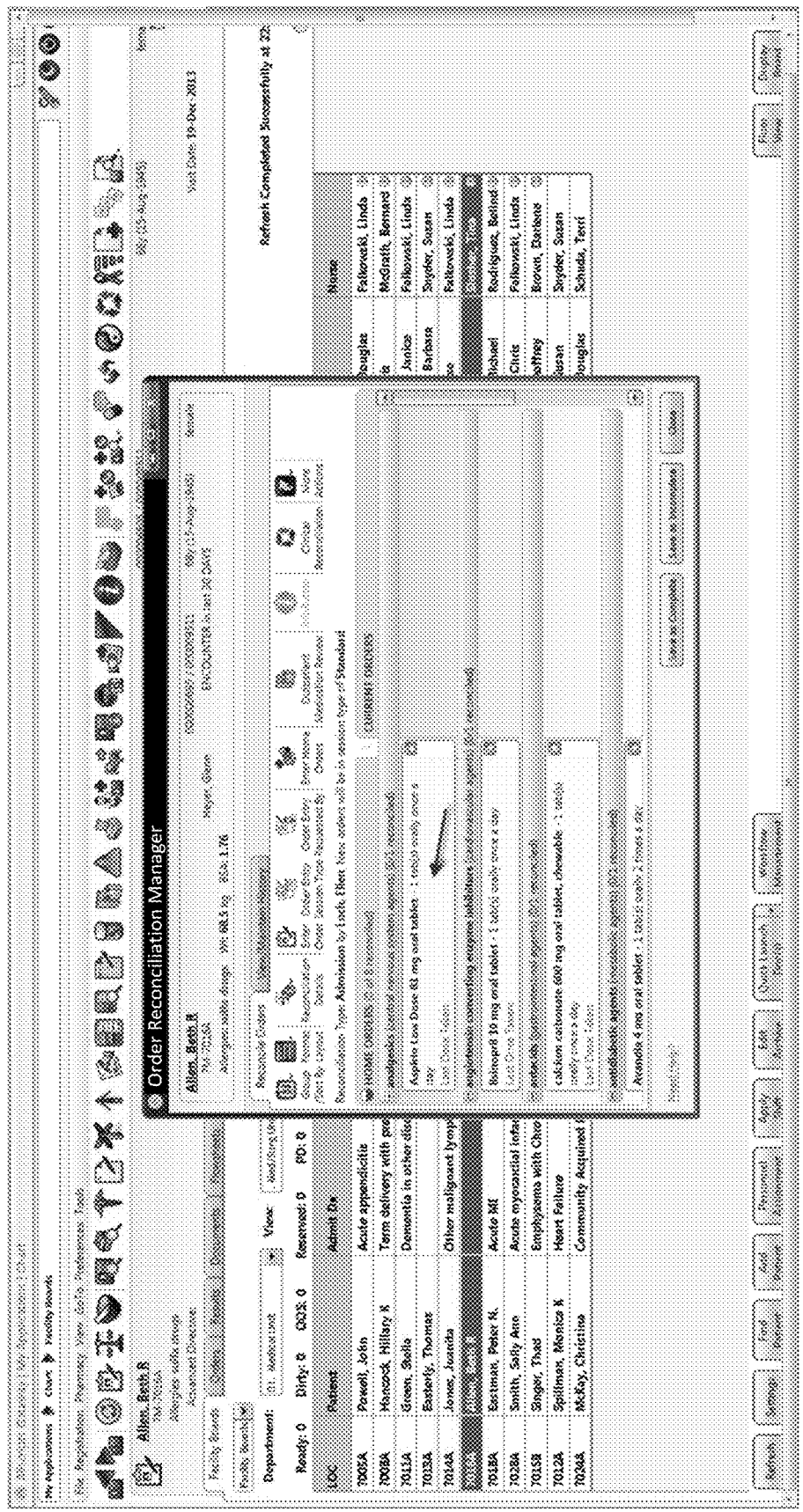
FIG. 35 illustrates an "Order Reconciliation Manager" user interface window for the selected patient in the user interface of FIG. 15.
Figure 36:
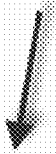
FIG. 36 illustrates just the "Order Reconciliation Manager" user interface window of FIG. 35 for clarity.
Figure 37:
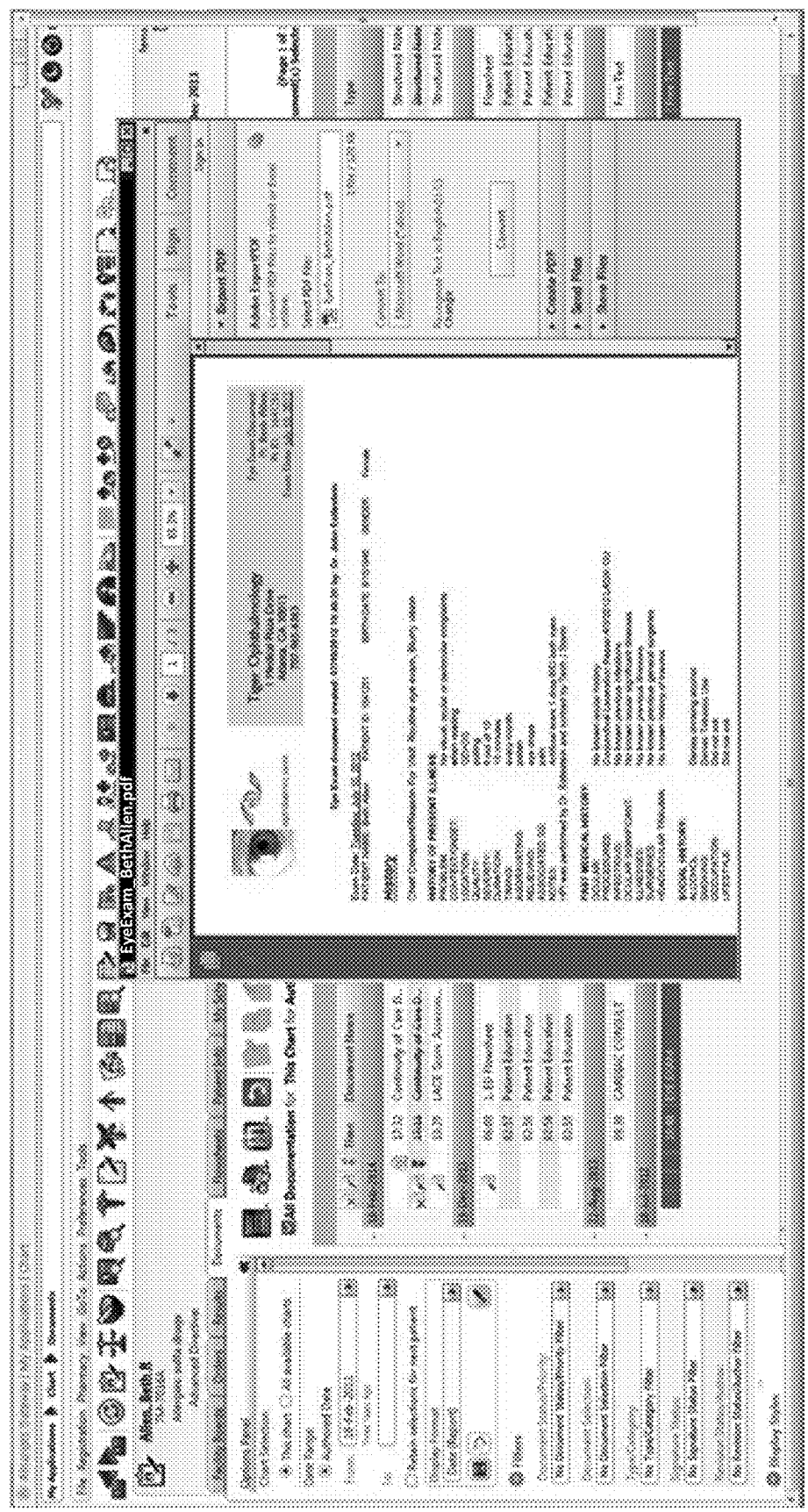
FIG. 37 illustrates a "Documents" tab view of the user interface window of FIG. 15, including an "Eye Exam" pdf document window providing a view of a document selected in such tab view.
Figure 38:
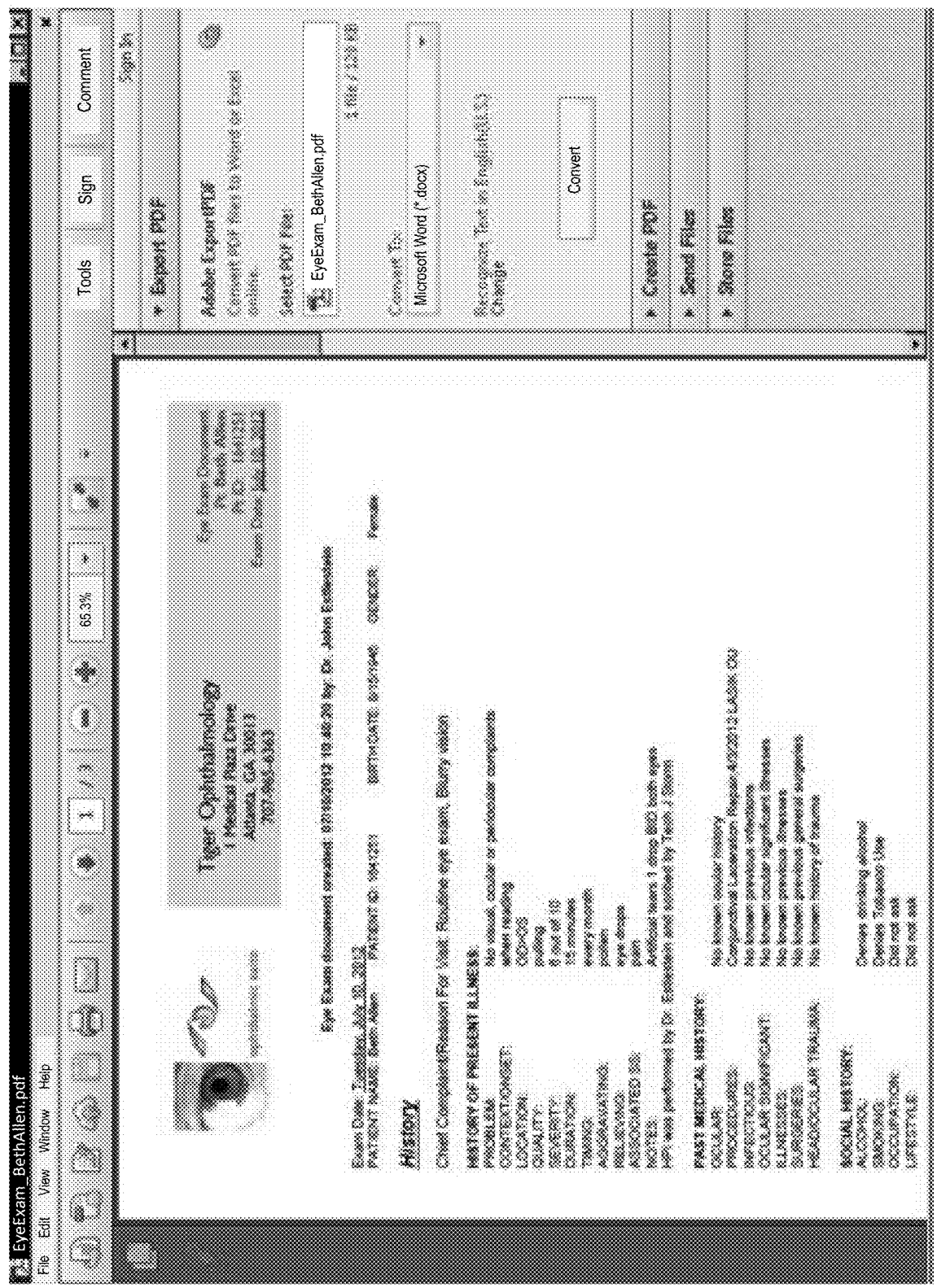
FIG. 38 illustrates just the "Eye Exam" pdf document window of FIG. 37 for clarity.

With respect to population health, joined data can be utilized with results and observations being shown in the various 'information widgets' seen in FIG. 13.

Figure 39:
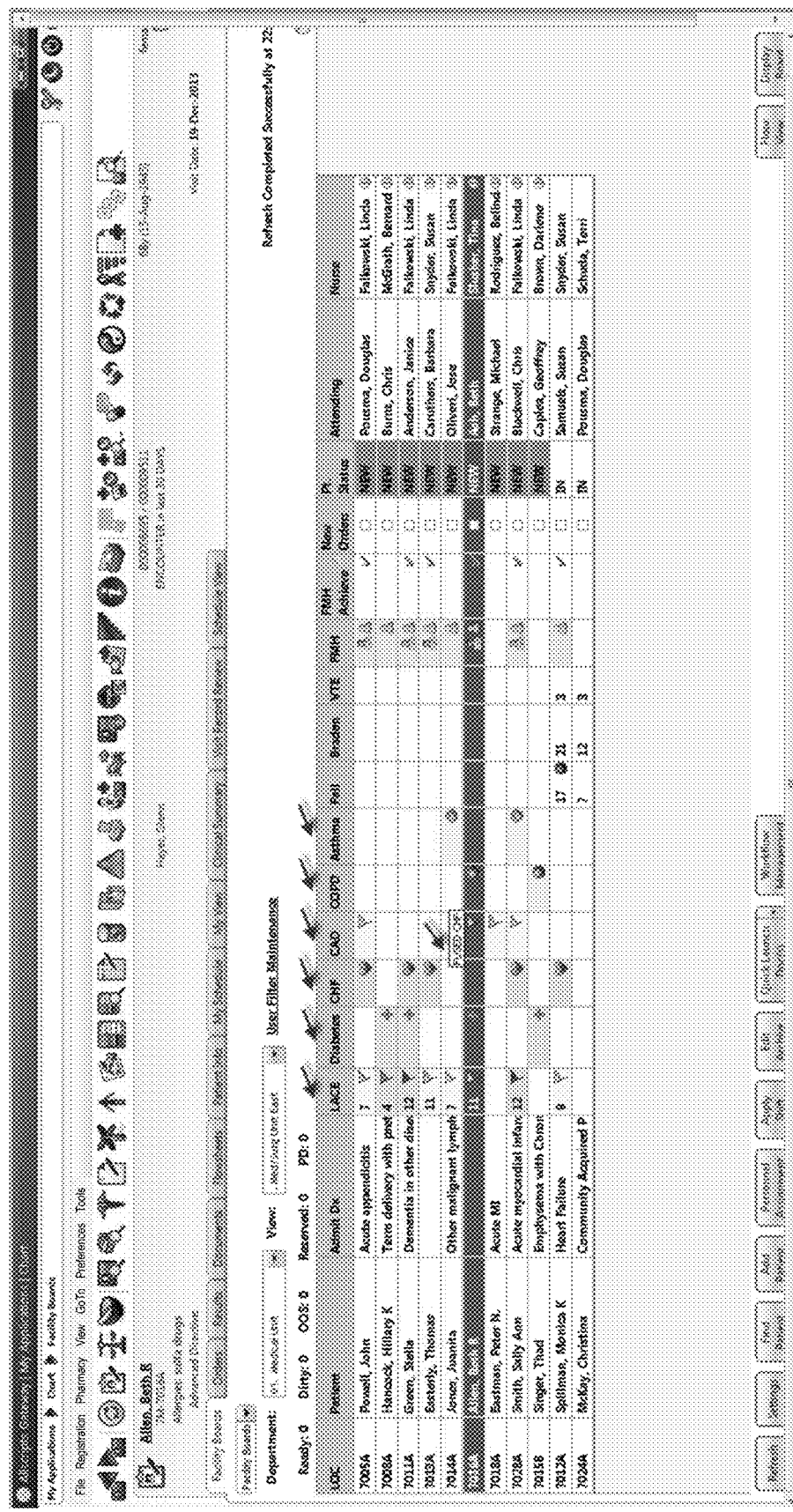
FIG. 39 illustrates another view of the "Facility Board" tab view within the overall context user interface window of the exemplary EHR software, similar to the view of FIG. 15.
Figure 40:
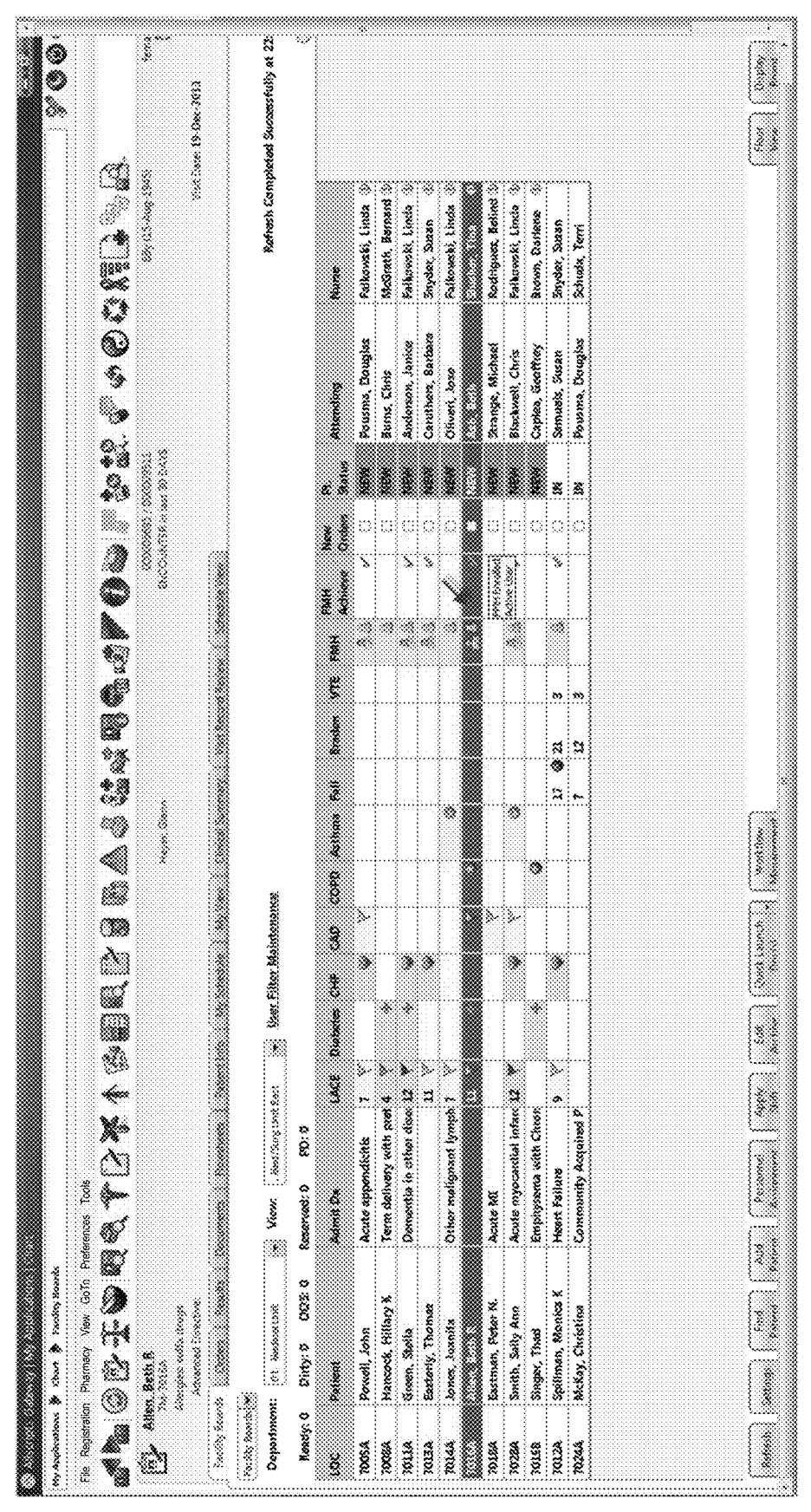

It will also be appreciated that the joined EHR data and community patient data can comprise healthcare documents, including PDF documents. Such documents are illustrated in FIGS. 39 and 40.

With general regard to the remaining figures not yet specifically addressed, these shown various screenshots of SCM wherein community patient data is presented and/or healthcare information and/or alerts are presented based on or as a function of such information.

For example, the community healthcare data for allergies, problems, medications, immunizations, documents, results, labs, observations, and encounters is presented in the native SCM forms with an indicator that the data is community healthcare data. This data can be viewed or acted upon in many ways. It can be used to alert healthcare providers to conditions at the point of care or be reconciled with SCM data and imported, and CDS alerts can be generated based on this data. Users can be notified at the time of viewing a patient's chart of the availability of the additional data with the ability to view and reconcile that data, all without having to manually select and import.

In addition, the retrieved community healthcare data preferably is presented in the SCM Clinical Summary tab for allergies, problems, encounters, medications, labs, and results. A notification preferably is made to a healthcare provider using the EHR software when a patient is selected in in the EHR software and community healthcare data for the selected patient is found. Furthermore, if the healthcare provider choses, he or she can view a user interface in which medication and allergy data can be reconciled. In this respect, patient-level record reconciliation can be performed.

Furthermore, as will now be appreciated, the community health data preferably is actionable in native SCM forms and clinical workflows with SCM data for allergies, medications, problems, and documents, for example.

Within the Documents Review user interface, clinicians can access critical documents obtained from the community, as illustrated in the drawings.

Exemplary workflows in SCM include, in this respect, the SCM Discharge Disposition Workflow; the Duplicate Order Alert Workflow; and the Drub-Allergy Interaction Alert Workflow. As will be appreciated, SCM alerting can and preferably is accomplished at the point of care using community health data retrieved by the DBMOTION software joined with the native EHR data. The SMC alerting preferably is performed for allergies, medications, encounters/visits, and results.

Additional information in the form of white papers relating to connective communities of care, health exchange information (HIE) entities, and related subject matter is contained in the Appendix to the specification submitted herewith, which is incorporated herein by reference.

The healthcare provider also preferably is shown the joined community healthcare data with the ability to pull selected joined community patient data into a patient's chart and, consequently, have that community patient data be saved in the patient's EHR in the EHR database at the point of clinical documentation, preferably through a structured notes interface as represented, for example, in FIGS. 23-28.

It should further be noted that, while many community health sources represent EHR systems of other healthcare organizations, medical providers, and other healthcare entities, one additional community source that is contemplated in one or more embodiments of the present invention is a database in which healthcare information is maintained by or on behalf of patients, rather than by or on behalf of healthcare providers. Such a database has been offered commercially in the past to patients (i.e., individual persons) as a consumer service by JARDOGS under the mark FOLLOW MY HEALTH (which is referenced in the drawings as FMH).

In closing, many benefits of one or more aspects of the invention are seen to be: just-in-time information for making important clinical decisions at the point-of-care; reduction of risk of human errors; increase in patient safety; dramatic reduction in gaps in care; improved care coordination; increased accountability of care; increased preventative care (screenings); increased trust; reduced clicks to view community-based healthcare information; avoidance of overwhelming data; reduction in costs of duplicative care; and enhanced clinical quality and reliability.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A computing device operated by a healthcare provider, the computing device comprising:
   a processor;
   a display; and
   memory storing electronic healthcare record (EHR) software, wherein the EHR software, when executed by the processor, is configured to cause the processor to perform acts comprising:
   responsive to receiving an identifier for a patient as input from the healthcare provider, retrieving, by the EHR software and by way of a network, EHR data for the patient from an EHR database comprising EHR data for a first plurality of patients, wherein the EHR data for the patient is formatted in a first data structure that has first fields;
   subsequent to retrieving the EHR data for the patient from the EHR database, retrieving, by the EHR software and by way of the network and based upon the identifier for the patient, community patient data for the patient from a community database comprising community patient data for a second plurality of patients, wherein the community patient data for the patient is formatted in a second data structure that has second fields;

converting, by the EHR software, the community patient data for the patient from being formatted in the second data structure to being formatted in the first data structure based upon field mappings that map the second fields of the second data structure to the first fields of the first data structure;

subsequent to converting the community patient data for the patient, combining, by the EHR software, the EHR data for the patient and the community patient data for the patient to form combined data, wherein the combining occurs without importing the community patient data for the patient into the EHR database, wherein each element in the combined data is assigned to the patient;

receiving, by the EHR software, a selection of a button in a graphical user interface (GUI) of the EHR software, wherein the GUI is shown on the display, and further wherein the button corresponds to a healthcare workflow for the patient; and responsive to receiving the selection of the button, presenting the combined data within the GUI to facilitate performance of the healthcare workflow, wherein the EHR data for the patient in the combined data is visually distinguished from the community patient data for the patient within the GUI of the EHR software.

2. The computing device of claim 1, wherein the community patient data for the second plurality of patients is a consolidation of a plurality of sources of electronic healthcare data maintained by different third parties.

3. The computing device of claim 1, wherein the healthcare workflow requires an order that has previously been documented within the community patient data for the patient, the acts further comprising:

presenting an alert within the GUI, wherein the alert indicates that the order is a duplicative order with the EHR data.

4. The computing device of claim 1, wherein the GUI comprises at least one of:

a facility boards user interface for managing patients at a healthcare facility;

a results user interface for accessing results;

a documents user interface for accessing documents;

a visit record review interface for reviewing prior patient encounters;

a structured notes interface for documenting a patient encounter;

a medication review user interface for reviewing medications of the patient; or an order reconciliation user interface for reviewing and writing orders for the patient.

5. The computing device of claim 1, wherein the healthcare workflow requires prescribing a medication.

6. The computing device of claim 1, the acts further comprising:

prior to combining the EHR data for the patient and the community patient data for the patient to form the combined data, identifying duplicative data between the EHR data for the patient and the community patient data for the patient; and preventing the duplicative data from being included in the combined data.

7. The computing device of claim 1, the acts further comprising:

executing an action in furtherance of the healthcare workflow using the combined data.

8. A method executed by a processor of a computing device while the processor executes electronic healthcare record (EHR) software, wherein the computing device is operated by a healthcare provider, the method comprising:

responsive to receiving an identifier for a patient as input from the healthcare provider, retrieving, by the EHR software and by way of a network, EHR data for the patient from an EHR database comprising EHR data for a first plurality of patients, wherein the EHR data for the patient is formatted in a first data structure that has first fields;

subsequent to retrieving the EHR data for the patient from the EHR database, retrieving, by the EHR software and by way of the network and based upon the identifier for the patient, community patient data for the patient from a community database comprising community patient data for a second plurality of patients, wherein the community patient data for the patient is formatted in a second data structure that has second fields;

converting, by the EHR software, the community patient data from being formatted in the second data structure to being formatted in the first data structure based upon field mappings that map the second fields of the second data structure to the first fields of the first data structure;

subsequent to converting the community patient data for the patient, combining, by the EHR software, the EHR data for the patient and the community patient data for the patient to form combined data, wherein the combining occurs without importing the community patient data for the patient into the EHR database, wherein each element in the combined data is assigned to the patient;

receiving, by the EHR software, a selection of a button in a graphical user interface (GUI) of the EHR software, wherein the GUI is shown on a display, and further wherein the button corresponds to a healthcare workflow for the patient; and responsive to receiving the selection of the button, presenting the combined data within the GUI of the EHR software to facilitate performance of the healthcare workflow, wherein the EHR data for the patient in the combined data is visually distinguished from the community patient data for the patient in the combined data within the GUI of the EHR software.

9. The method of claim 8, wherein the community patient data for the second plurality of patients is a consolidation of a plurality of sources of electronic healthcare data maintained by different third parties.

10. The method of claim 8, wherein the healthcare workflow requires an order that has previously been documented within the community patient data for the patient, the method further comprising:

presenting an alert within the GUI, wherein the alert indicates that the order is a duplicative order with the EHR data.

11. The method of claim 8, wherein the GUI comprises at least one of:

a facility boards user interface for managing patients at a healthcare facility;

a results user interface for accessing results;

a documents user interface for accessing documents;

a visit record review interface for reviewing prior patient encounters;

a structured notes interface for documenting a patient encounter;

a medication review user interface for reviewing medications of the patient; or an order reconciliation user interface for reviewing and writing orders for the patient.

12. The method of claim 8, wherein the community patient data for the plurality of patients is a consolidation of a plurality of sources of electronic healthcare data maintained by different third parties.

13. A computer-readable storage medium comprising electronic healthcare record (EHR) software that, when executed by a processor of a computing device operated by a healthcare provider, causes the processor to perform acts comprising:

responsive to receiving an identifier for a patient as input from the healthcare provider, retrieving, by the EHR software and by way of a network, EHR data for the patient from an EHR database comprising EHR data for a first plurality of patients, wherein the EHR data for the patient is formatted in a first data structure that has first fields;

subsequent to retrieving the EHR data for the patient from the EHR database, retrieving, by the EHR software and by way of the network and based upon the identifier for the patient, community patient data for the patient from a community database comprising community patient data for a second plurality of patients, wherein the community patient data for the patient is formatted in a second data structure that has second fields;

converting, by the EHR software, the community patient data for the patient from being formatted in the second data structure to being formatted in the first data structure based upon field mappings that map the second fields of the second data structure to the first fields of the first data structure;

subsequent to converting the community patient data for the patient, combining, by the EHR software, the EHR data for the patient and the community patient data for the patient to form combined data, wherein the combining occurs without importing the community patient data for the patient into the EHR database, wherein each element in the combined data is assigned to the patient;

receiving, by the EHR software, a selection of a button in a graphical user interface (GUI) of the EHR software, wherein the GUI is shown on a display, and further wherein the button corresponds to a healthcare workflow for the patient; and responsive to receiving the selection of the button, presenting the combined data within the GUI of the EHR software to facilitate performance of the healthcare workflow, wherein the EHR data for the patient in the combined data is visually distinguished from the community patient data for the patient in the combined data within the GUI of the EHR software.

14. The computer-readable storage medium of claim 13, wherein the community patient data for the second plurality of patients is a consolidation of a plurality of sources of electronic healthcare data maintained by different third parties.

15. The computer-readable storage medium of claim 13, the acts further comprising:

subsequent to a pre-determined period of time elapsing, retrieving, by the EHR software and by way of the network, second community patient data for the patient from the community database, wherein the second community patient data is formatted in the second data structure that has the second fields;

converting, by the EHR software, the second community patient data for the patient from being formatted in the second data structure to being formatted in the first data structure based upon the field mappings that map the second fields of the second data structure to the first fields of the first data structure;

subsequent to converting the second community patient data for the patient, combining the second community patient data for the patient with the combined data to form second combined data, wherein the combining occurs without importing the second community patient data for the patient into the EHR database, wherein each element in the second combined data is assigned to the patient; and presenting the second combined data within the GUI of the EHR software, wherein the EHR data for the patient in the combined data, the community patient data for the patient in the combined data, and the second community patient data for the patient in the combined data are visually distinguished within the GUI of the EHR software.

16. The computer-readable storage medium of claim 13, wherein the healthcare workflow requires an order that has previously been documented within the community patient data for the patient, the acts further comprising:

presenting an alert within the GUI, wherein the alert indicates that the order is a duplicative order with the EHR data.

17. The computer-readable storage medium of claim 13, wherein the GUI comprises at least one of:

a facility boards user interface for managing patients at a healthcare facility;

a results user interface for accessing results;

a documents user interface for accessing documents;

a visit record review interface for reviewing prior patient encounters;

a structured notes interface for documenting a patient encounter;

a medication review user interface for reviewing medications of the patient; or an order reconciliation user interface for reviewing and writing orders for the patient.

* * * * *